US010682305B2

(12) United States Patent
Herrlein et al.

(10) Patent No.: US 10,682,305 B2
(45) Date of Patent: *Jun. 16, 2020

(54) COMPOSITION FOR PROVIDING A FILM ON KERATIN FIBRES

(71) Applicant: Noxell Corporation, Hunt Valley, MD (US)

(72) Inventors: Mathias Kurt Herrlein, Kronberg (DE); Tatjana Schaefer, Butzbach (DE); Andreas Flohr, Kronberg (DE); Marianna Forgione, Schwalbach am Taunus (DE); Matija Crne, Schwalbach am Taunus (DE); Yonus Gizaw, West Chester, OH (US); Ursula Christina Glaser, Wiesbaden (DE)

(73) Assignee: Noxell Corporation, Hunt Valley, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/042,467

(22) Filed: Feb. 12, 2016

(65) Prior Publication Data
US 2016/0235653 A1  Aug. 18, 2016

(30) Foreign Application Priority Data
Feb. 17, 2015  (EP) .................................... 15155380

(51) Int. Cl.
| A61Q 5/06  | (2006.01) |
| A61K 8/898 | (2006.01) |
| A61K 8/89  | (2006.01) |
| A61K 8/02  | (2006.01) |
| A61K 8/73  | (2006.01) |
| A61K 8/33  | (2006.01) |
| A61K 8/891 | (2006.01) |
| A61K 8/86  | (2006.01) |

(52) U.S. Cl.
CPC ............ A61K 8/898 (2013.01); A61K 8/0241 (2013.01); A61K 8/33 (2013.01); A61K 8/731 (2013.01); A61K 8/86 (2013.01); A61K 8/89 (2013.01); A61K 8/891 (2013.01); A61Q 5/065 (2013.01)

(58) Field of Classification Search
None
See application file for complete search history.

(56) References Cited

U.S. PATENT DOCUMENTS

| 4,192,862 A | 3/1980 | Pengilly |
| 5,567,428 A | 10/1996 | Hughes |
| 5,753,216 A | 5/1998 | Leitch et al. |
| 6,451,747 B1 | 9/2002 | Decoster |
| 8,597,670 B2 | 12/2013 | Allwyn et al. |
| 8,999,310 B1 | 4/2015 | Frank et al. |
| 9,844,499 B2 * | 12/2017 | Herrlein ................ A61Q 5/10 |
| 10,045,931 B2 | 8/2018 | Herrlein et al. |
| 10,406,093 B2 | 9/2019 | Herrlein et al. |
| 2003/0140429 A1 | 7/2003 | Legrand et al. |
| 2003/0147827 A1 | 8/2003 | DeCoster et al. |
| 2003/0211953 A1 | 11/2003 | Glenn et al. |
| 2003/0223946 A1 | 12/2003 | Glenn et al. |
| 2004/0010863 A1 | 1/2004 | Gawtrey et al. |
| 2004/0018163 A1 | 1/2004 | Yu |
| 2004/0045098 A1 | 3/2004 | Lazzeri |
| 2005/0095212 A1 | 5/2005 | Hirano |
| 2005/0132506 A1 | 6/2005 | McKelvey |
| 2005/0196372 A1 | 9/2005 | Cajan et al. |
| 2006/0041026 A1 | 2/2006 | Mahr et al. |
| 2006/0265818 A1 * | 11/2006 | Seiler ...................... A61K 8/33 |
| | | 8/412 |
| 2007/0039103 A1 | 2/2007 | Godfrey |
| 2007/0253987 A1 | 11/2007 | Wozniak et al. |
| 2008/0043233 A1 | 2/2008 | Snabre et al. |
| 2009/0068135 A1 | 3/2009 | Glenn et al. |
| 2009/0074702 A1 | 3/2009 | Allard et al. |
| 2009/0081143 A1 | 3/2009 | Mammone et al. |
| 2009/0226381 A1 | 9/2009 | Maillefer et al. |
| 2010/0037404 A1 | 2/2010 | Koike et al. |
| 2011/0067723 A1 | 3/2011 | Bureiko et al. |
| 2011/0104094 A1 | 5/2011 | Lee et al. |
| 2011/0110990 A1 | 5/2011 | Yu |
| 2011/0174329 A1 | 7/2011 | Seng et al. |
| 2011/0229429 A1 * | 9/2011 | Hoffmann ................ A61K 8/19 |
| | | 424/70.9 |
| 2012/0071382 A1 | 3/2012 | Wang et al. |
| 2012/0093755 A1 | 4/2012 | Humphreys et al. |
| 2012/0201774 A1 | 8/2012 | Schweinsberg et al. |

(Continued)

FOREIGN PATENT DOCUMENTS

| CN | 107223050 A | 9/2017 |
| CN | 107249551 A | 10/2017 |

(Continued)

OTHER PUBLICATIONS

"U.S. Appl. No. 15/042,488, Non Final Office Action dated Apr. 20, 2017", 25 pgs.
"U.S. Appl. No. 15/042,488, Response filed Mar. 2, 2017 to Restriction Requirement dated Nov. 3, 2016", 7 pgs.
"U.S. Appl. No. 15/042,488, Response filed Oct. 19, 2017 to Non Final Office Action dated Apr. 20, 2017", 11 pgs.
"U.S. Appl. No. 15/042,488, Restriction Requirement dated Nov. 3, 2016", 9 pgs.
"U.S. Appl. No. 15/042,519, Restriction Requirement dated Jun. 6, 2017", 8 pgs.

(Continued)

Primary Examiner — Jyothsna A Venkat
(74) Attorney, Agent, or Firm — Schwegman Lundberg & Woessner, P.A.

(57) ABSTRACT

A composition for providing a film on keratin fibres comprises: a film-forming aminosilicone polymer; a silicone resin which is a MQ resin; a thickening system comprising a deposition enhancer and a thickening polymer; and a solvent. Also, associated methods, kits and uses are provided.

6 Claims, 1 Drawing Sheet

(56) References Cited

U.S. PATENT DOCUMENTS

| | | |
|---|---|---|
| 2012/0328550 A1 | 12/2012 | De Boni et al. |
| 2013/0061866 A1 | 3/2013 | Klingelmeyer et al. |
| 2013/0098384 A1 | 4/2013 | Uellner |
| 2013/0147827 A1 | 6/2013 | Kurkure et al. |
| 2013/0149358 A1 | 6/2013 | Colaco et al. |
| 2013/0177517 A1 | 7/2013 | Merget et al. |
| 2014/0044762 A1 | 2/2014 | Colaco et al. |
| 2015/0164196 A1 | 6/2015 | Teboul et al. |
| 2015/0174051 A1 | 6/2015 | Teboul |
| 2016/0015622 A1 | 1/2016 | Rafferty et al. |
| 2016/0235654 A1 | 8/2016 | Herrlein et al. |
| 2016/0235655 A1 | 8/2016 | Herrlein et al. |
| 2016/0235656 A1 | 8/2016 | Herrlein et al. |
| 2016/0235657 A1 | 8/2016 | Herrlein et al. |
| 2016/0235658 A1 | 8/2016 | Herrlein et al. |
| 2016/0310378 A1 | 10/2016 | Herrlein et al. |
| 2018/0303745 A1 | 10/2018 | Herrlein et al. |

FOREIGN PATENT DOCUMENTS

| | | |
|---|---|---|
| CN | 107249559 A | 10/2017 |
| CN | 107249562 A | 10/2017 |
| CN | 107278148 A | 10/2017 |
| CN | 107278150 A | 10/2017 |
| CN | 107427427 A | 12/2017 |
| EP | 0000664 A1 | 2/1979 |
| EP | 1084696 A1 | 3/2001 |
| EP | 1356800 A2 | 10/2003 |
| EP | 1543820 A1 | 6/2005 |
| EP | 1570833 A1 | 9/2005 |
| EP | 2090295 A1 | 8/2009 |
| EP | 2105127 A1 | 9/2009 |
| EP | 2431421 A1 | 3/2012 |
| EP | 1419759 B1 | 12/2012 |
| JP | 0859994 A | 3/1996 |
| JP | H0859994 A | 3/1996 |
| JP | 2003081783 A | 3/2003 |
| JP | 2003160446 A | 6/2003 |
| JP | 2003342137 A | 12/2003 |
| JP | 2008538768 A | 11/2008 |
| JP | 2009057380 A | 3/2009 |
| JP | 2010275279 A | 12/2010 |
| JP | 2011511830 A | 4/2011 |
| JP | 2011511842 A | 4/2011 |
| JP | 2013514274 A | 4/2013 |
| MX | 363736 B | 4/2019 |
| WO | WO-03086333 A1 | 10/2003 |
| WO | WO-2008/084442 A1 | 7/2008 |
| WO | WO2011128255 | 10/2011 |
| WO | WO-2013/085577 A2 | 6/2013 |
| WO | WO-2014/001391 A1 | 1/2014 |
| WO | WO-2014/137859 A1 | 9/2014 |
| WO | WO-2016/133806 A1 | 8/2016 |
| WO | WO-2016/133807 A1 | 8/2016 |
| WO | WO-2016/133808 A1 | 8/2016 |
| WO | WO-2016/133809 A1 | 8/2016 |
| WO | WO-2016/133810 A1 | 8/2016 |
| WO | WO-2016/133812 A1 | 8/2016 |
| WO | WO-2016133811 A1 | 8/2016 |

OTHER PUBLICATIONS

"U.S. Appl. No. 15/042,545, Final Office Action dated Jun. 23, 2017", 29 pgs.
"U.S. Appl. No. 15/042,545, Non Final Office Action dated Sep. 22, 2016", 17 pgs.
"U.S. Appl. No. 15/042,545, Response filed Feb. 23, 2017 to Non Final Office Action dated Sep. 22, 2016", 9 pgs.
"U.S. Appl. No. 15/042,545, Response filed Oct. 23, 2017 to Final Office Action dated Jun. 23, 2017", 10 pgs.
"U.S. Appl. No. 15/042,557, Non Final Office Action dated Aug. 11, 2017", 23 pgs.
"U.S. Appl. No. 15/042,557, Response filed Aug. 1, 2017 to Restriction Requirement dated Mar. 1, 2017", 6 pgs.
"U.S. Appl. No. 15/042,557, Restriction Requirement dated Mar. 1, 2017", 7 pgs.
"U.S. Appl. No. 15/042,596 Response filed Jul. 21, 2017 to Non Final Office Action dated Jan. 11, 2017", 11 pgs.
"U.S. Appl. No. 15/042,596, Non Final Office Action dated Jan. 11, 2017", 16 pgs.
"U.S. Appl. No. 15/042,596, Response filed Sep. 12, 2016 to Restriction Requirement dated Jul. 12, 2016", 5 pgs.
"U.S. Appl. No. 15/042,596, Restriction Requirement dated Jul. 12, 2016", 7 pgs.
"European Application Serial No. 16155384.7, Extended European Search Report dated May 4, 2016", 11 pgs.
"European Application Serial No. 16155384.7, Office Action dated Aug. 29, 2016", 2 pgs.
"European Application Serial No. 16155384.7, Response filed Feb. 24, 2017 to Office Action dated Aug. 29, 2016", 4 pgs.
"European Application Serial No. 16155385.4, Extended European Search Report dated May 13, 2016", 12 pgs.
"European Application Serial No. 16155385.4, Office Action dated Aug. 29, 2016", 2 pgs.
"European Application Serial No. 16155385.4, Response filed Feb. 24, 2017 to Office Action dated Aug. 29, 2016", 7 pgs.
"European Application Serial No. 16155387.0, Extended European Search Report dated May 4, 2016", 12 pgs.
"European Application Serial No. 16155387.0, Office Action dated Aug. 29, 2016", 2 pgs.
"European Application Serial No. 16155387.0, Response filed Feb. 24, 2017 to Office Action dated Aug. 29, 2016", 4 pgs.
"European Application Serial No. 16155391.2, Communication Pursuant to Article 94(3) EPC dated Jul. 18, 2017", 6 pgs.
"European Application Serial No. 16155391.2, Extended European Search Report dated Apr. 15, 2016", 11 pgs.
"European Application Serial No. 16155391.2, Office Action dated Aug. 29, 2016", 2 pgs.
"European Application Serial No. 16155391.2, Response filed Fe. 24, 2017 to Office Action dated Aug. 29, 2016", 4 pgs.
"European Application Serial No. 16155398.7 Response filed Feb. 24, 2017 to Communication pursuant to Rule 69 EPC and Invitation pursuant to Rule 70a(1) EPC dated Aug. 29, 2016", 4 pgs.
"European Application Serial No. 16155398.7, Communication Pursuant to Article 94(3) EPC dated Jul. 17, 2017", 4 pgs.
"European Application Serial No. 16155398.7, Extended European Search Report dated Mar. 20, 2016", 11 pgs.
"European Application Serial No. 16155400.1, Extended European Search Report dated May 4, 2016", 13 pgs.
"European Application Serial No. 16155400.1, Response filed Feb. 24, 2017 to Extended European Search Report dated May 4, 2016", 13 pgs.
"International Application Serial No. PCT/US2016/017716, International Preliminary Report on Patentability dated Aug. 31, 2017", 10 pgs.
"International Application Serial No. PCT/US2016/017718, International Preliminary Report on Patentability dated Aug. 31, 2017", 11 pgs.
"International Application Serial No. PCT/US2016/017718, International Search Report dated May 3, 2016", 5 pgs.
"International Application Serial No. PCT/US2016/017718, Written Opinion dated May 3, 2016", 9 pgs.
"International Application Serial No. PCT/US2016/017720, International Preliminary Report on Patentability dated Aug. 31, 2017", 9 pgs.
"International Application Serial No. PCT/US2016/017720, International Search Report and Written Opinion dated May 3, 2016", 13 pgs.
"International Application Serial No. PCT/US2016/017720, International Search Report dated May 3, 2016", 6 pgs.
"International Application Serial No. PCT/US2016/017720, Written Opinion dated May 3, 2016", 7 pgs.
"International Application Serial No. PCT/US2016/017725, International Preliminary Report on Patentability dated Aug. 31, 2017", 9 pgs.
"International Application Serial No. PCT/US2016/017725, International Search Report dated May 9, 2016", 6 pgs.

(56) References Cited

OTHER PUBLICATIONS

"International Application Serial No. PCT/US2016/017725, Written Opinion dated May 9, 2016", 7 pgs.
"International Application Serial No. PCT/US2016/017729, International Preliminary Report on Patentability dated Aug. 31, 2017", 10 pgs.
"International Application Serial No. PCT/US2016/017729, International Search Report dated Apr. 19, 2016", 4 pgs.
"International Application Serial No. PCT/US2016/017729, Written Opinion dated Apr. 19, 2016", 8 pgs.
"International Application Serial No. PCT/US2016/017735, International Preliminary Report on Patentability dated Aug. 31, 2017", 10 pgs.
"International Application Serial No. PCT/US2016/017735, International Search Report dated May 3, 2016", 4 pgs.
"International Application Serial No. PCT/US2016/017735, Written Opinion dated May 3, 2016", 8 pgs.
Barber, David, et al., "A Logical Stepwise Approach to Laser Diffraction Particle Size Distribution Analysis Methods Development and Validation", Pharmaceutical Development and Technology, 3(2), (1998), 153-161.
Brun, A., et al., "Film formation of coatings studied by diffusing-wave spectroscopy", Progress in Organic Coatings, 61, (2008), 181-191.
Dihang, H., et al., "Film formation analysis by optical methods", Technical Update, Surface Coatings International, Issue 2008/X, 1-4.
Wacker, Chemie AG, "Produktsuche—Belsil", [online]. [Retrieved on May 3, 2015], Retrieved from the Internet: <URL: http://web.archive.org/web/20150503100844/ http://www.wacker.com/cms/de/products/productsearch/product-search.jsp>, (May 5, 2015), 1 pg.
"U.S. Appl. No. 15/042,488, Final Office Action dated Nov. 8, 2017", 27 pgs.
"U.S. Appl. No. 15/042,519, Response filed Nov. 6, 2017 to Restriction Requirement dated Jun. 6, 2017", 6 pgs.
"U.S. Appl. No. 15/042,557, Response filed Nov. 9, 2017 to Non-Final Office Action dated Aug. 11, 2017", 14 pgs.
"European Application Serial No. 16155384.7, Communication Pursuant to Article 94(3) EPC dated Nov. 9, 2017", 5 pgs.
"European Application Serial No. 16155385.4, Communication Pursuant to Article 94(3) EPC dated Nov. 9, 2017", 6 pgs.
"U.S. Appl. No. 15/042,488, Advisory Action dated Apr. 5, 2018", 5 pgs.
"U.S. Appl. No. 15/042,488, Examiner Interview Summary dated Aug 31, 2018", 3 pgs.
"U.S. Appl. No. 15/042,488, Non Final Office Action dated Aug. 2, 2018", 25 pgs.
"U.S. Appl. No. 15/042,488, Response filed Mar. 6, 2018 to Final Office Action dated Nov. 8, 2017", 10 pgs.
"U.S. Appl. No. 15/042,488, Response filed Apr. 6, 2018 to Final Office Action dated Nov. 8, 2017", 10 pgs.
"U.S. Appl. No. 15/042,519, Non Final Office Action dated Dec. 15, 2017", 7 pgs.
"U.S. Appl. No. 15/042,519, Response filed Jun. 15, 2018 to Non Final Office Action dated Dec. 15, 2017", 9 pgs.
"U.S. Appl. No. 15/042,545, Non Final Office Action dated Jan. 12, 2018", 29 pgs.
"U.S. Appl. No. 15/042,545, Response filed Jun. 12, 2018 to Non Final Office Action dated Jan. 12, 2018", 13 pgs.
"U.S. Appl. No. 15/042,557, Final Office Action dated Jan. 16, 2018", 18 pgs.
"U.S. Appl. No. 15/042,557, Non Final Office Action dated Jul. 30, 2018", 20 pgs.
"U.S. Appl. No. 15/042,557, Response filed Jul. 13, 2018 to Final Office Action dated Jan. 16, 2018", 10 pgs.
"U.S. Appl. No. 15/042,596, Final Office Action dated Dec. 27, 2017", 17 pgs.
"U.S. Appl. No. 15/042,596, Notice of Allowance dated Mar. 30, 2018", 11 pgs.
"U.S. Appl. No. 15/042,596, Response filed Feb. 27, 2018 to Final Office Action dated Dec. 27, 2017", 9 pgs.
"U.S. Appl. No. 16/022,163, Preliminary Amendment filed Jun. 29, 2018", 7 pgs.
"European Application Serial No. 16155384.7, Response filed May 3, 2018 to Communication Pursuant to Article 94(3) EPC dated Nov. 9, 2017", 13 pgs.
"European Application Serial No. 16155385.4, Response filed May 11, 2018 to Communication Pursuant to Article 94(3) EPC dated Nov. 9, 2017", w/ English Claims, 14 pgs.
"European Application Serial No. 16155391.2, Response filed Jan. 26, 2018 to Communication Pursuant to Article 94(3) EPC dated Jul. 18, 2017", w/ Amended Claims, 26 pgs.
"European Application Serial No. 16155398.7, Communication Pursuant to Article 94(3) EPC dated Jul. 19, 2018", 5 pgs.
"European Application Serial No. 16155398.7, Response filed Nov. 27, 2017 to Communication Pursuant to Article 94(3) EPC dated Jul. 17, 2017", 14 pgs.
"European Application Serial No. 16155400.1, Communication Pursuant to Article 94(3) EPC dated Mar. 1, 2018", 4 pgs.
"European Application Serial No. 16155400.1, Response filed Jul. 16, 2018 to Communication Pursuant to Article 94(3) EPC dated Mar. 1, 2018", 3 pgs.
"Quatemium-18 Bentonite", Cosmetics Info (Online), URL: https://cosmeticsinfo.org/ingredient/quaternium-18-bentonite, (accessed Aug. 6, 2018), 2 pgs.
Nair, "Final report on the safety assessment of Benzyl Alcohol, Benzoic Acid, and Sodium Benzoate", Int J Toxicol.; vol. 20, Suppl. 3, (2001), 23-50.
"European Application Serial No. 16155384.7, Communication Pursuant to Article 94(3) EPC dated Nov. 19, 2018", 4 pgs.
"European Application Serial No. 16155385.4, Communication Pursuant to Article 94(3) EPC dated Nov. 19, 2018", 5 pgs.
"European Application USerial No. 16155398.7, Response filed Nov. 29, 2018 to Communication Pursuant to Article 94(3) EPC dated Jul. 19, 2018", w/ English Claims, 12 pgs.
"U.S. Appl. No. 15/042,488, Response filed Oct. 31, 2018 to Non Final Office Action dated Aug. 2, 2018", 9 pgs.
"U.S. Appl. No. 15/042,519, Final Office Action dated Dec. 18, 2018", 13 pgs.
"U.S. Appl. No. 15/042,545, Final Office Action dated Oct. 4, 2018", 21 pgs.
"U.S. Appl. No. 15/042,557, Final Office Action dated Nov. 30, 2018", 20 pgs.
"U.S. Appl. No. 15/042,557, Response filed Oct. 30, 2018 to Non Final Office Action dated Jul. 30, 2018", 12 pgs.
"Polydimethylsiloxane Product Information", FAO JECFA Monographs 5, [Online] Retrieved from the internet: <http://www.fao.org/fileadmin/user_upload/jecfa_additives/docs/monograph5/additive-315-m5.pdf>, (2008), 5 pgs.
Chung-Feng, Jeffrey Kuo, et al., "Silicone resin synthesized by tetraethoxysilane and chlorotrimethylsilane through hydrolysis-condensation reaction", Journal of Applied Polymer Science, (2014), 8 pgs.
"U.S. Appl. No. 15/042,488, Response filed Apr. 3, 2019 to Final Office Action dated Jan. 3, 2019", 12 pgs.
"U.S. Appl. No. 15/042,519, Response filed Mar. 18, 2019 to Final Office Action dated Dec. 18, 2018", 10 pgs.
"U.S. Appl. No. 15/042,545, Notice of Allowance dated Mar. 22, 2019", 9 pgs.
"U.S. Appl. No. 15/042,545, Response filed Jan. 29, 2019 to Final Office Action dated Oct. 4, 2018", 17 pgs.
"U.S. Appl. No. 15/042,557, Non Final Office Action dated Apr. 1, 2019", 19 pgs.
"U.S. Appl. No. 15/042,557, Response filed Feb. 22, 2019 to Final Office Action dated Nov. 30, 2018", 10 pgs.
"European Application Serial No. 16155391.2, Response Filed Mar. 6, 2019 to Communication Pursuant to Article 94(3) EPC dated Jul. 19, 2018", 13 pgs.
"U.S. Appl. No. 15/042,488, Final Office Action dated Jan. 3, 2019", 25 pgs.
"European Application Serial No. 16155391.2, Communication Pursuant to Article 94(3) EPC dated Jul. 19, 2018", 4 pgs.

(56) References Cited

OTHER PUBLICATIONS

"U.S. Appl. No. 15/042,557, Non Final Office Action dated Jan. 7, 2020", 19 pgs.
"U.S. Appl. No. 15/042,577, Notice of Allowance dated Aug. 15, 2017", 8 pgs.
"U.S. Appl. No. 15/042,577, Response filed Jun. 9, 2017 to Restriction Requirement dated Dec. 9, 2016", 7 pgs.
"U.S. Appl. No. 15/042,577, Restriction Requirement dated Dec. 9, 2016", 8 pgs.
"European Application Serial No. 15155399.7, Communication Pursuant to Article 94(3) EPC dated Jan. 2, 2020", 5 pgs.
"European Application Serial No. 16155394.6, Extended European Search Report dated may 3, 2016", 9 pgs.
"European Application Serial No. 16155394.6, Response filed Feb. 24, 2017 to European Search Report and Office Action dated Aug. 29, 2016", 3 pgs.
"European Application Serial No. 16155398.7, Communication Pursuant to Article 94(3) EPC dated Jan. 2, 2020", 5 pgs.
"International Application Serial No. PCT/US2016/017732, International Search Report dated May 9, 2016", 4 pgs.
"International Application Serial No. PCT/US2016/017732, Written Opinion dated May 9, 2016", 7 pgs.
"Japanese Application Serial No. 2017-542370, Notice of Reasons for Rejection dated Jan. 7, 2020", w/ English Translation, 15 pgs.
"Japanese Application Serial No. 2017-542371, Notice of Reasons for Rejection dated Jan. 7, 2020", w/ English Translation, 15 pgs.
"Japanese Application Serial No. 2017-542379, Notification of Reasons for Refusal dated Jan. 7, 2020", w/ English Translation, 13 pgs.
"U.S. Appl. No. 15/042,488, Final Office Action dated Sep. 23, 2019", 27 pgs.
"U.S. Appl. No. 15/042,488, Non Final Office Action dated Jun. 3, 2019", 28 pgs.
"U.S. Appl. No. 15/042,488, Response filed Aug. 26, 2019 to Non-Final Office Action dated Jun. 3, 2019", 10 pgs.
"U.S. Appl. No. 15/042,519, Non Final Office Action dated Jul. 11, 2019", 12 pgs.
"U.S. Appl. No. 15/042,545, Corrected Notice of Allowability dated Aug. 9, 2019", 2 pgs.
"U.S. Appl. No. 15/042,557, Final Office Action dated Aug. 13, 2019", 20 pgs.
"U.S. Appl. No. 15/042,557, Response filed Jul. 26, 2019 to Non-Final Office Action dated Apr. 1, 2019", 10 pgs.
"U.S. Appl. No. 16/022,163, Non Final Office Action dated Jun. 27, 2019", 10 pgs.
"U.S. Appl. No. 16/022,163, Response filed Jul. 23, 2019 to Non-Final Office Action dated Jun. 27, 2019", 7 pgs.
"European Application Serial No. 16155384.7, Response filed May 15, 2019 to Communication Pursuant to Article 94(3) EPC dated Nov. 19, 2018", W/ English Claims, 16 pgs.
"European Application Serial No. 16155385.4, Response filed May 14, 2019 to Communication Pursuant to Article 94(3) EPC dated Nov. 19, 2018", w/ English Claims, 16 pgs.
"Keratin", Encyclopedia Britannica, Inc., [Online] Retrieved from the internet: <URL: https://www.britannica.com/print/article/315321>,(Jan. 11, 2019), 2 pgs.
"Mexican Application Serial No. MX/a/2017/010512, Office Action dated Jul. 12, 2019", w/o English Translation, 6 pgs.
"Mexican Application Serial No. MX/a/2017/010513, Office Action dated Apr. 5, 2019", w/o English Translation, 5 pgs.
"Mexican Application Serial No. MX/a/2017/010513, Response Filed Jul. 1, 2019 Office Action dated Apr. 5, 2019", w/ English Claims, 13 pgs.
"Mexican Application Serial No. MX/a/2017/010609, Office Action dated Apr. 30, 2019", w/o English Translation, 5 pgs.
"Mexican Application Serial No. MX/a/2017/010609, Office Action dated Aug. 29, 2019", w/o English Translation, 6 pgs.
"Mexican Application Serial No. MX/a/2017/010610, Office Action dated May 3, 2019", w/o English Translation, 5 pgs.

"Mexican Application Serial No. MX/a/2017/010610, Office Action dated Sep. 3, 2019", w/o English Translation, 6 pgs.
"SiSiB Silicone Resins", [Online] Retrieved from the internet on Jun. 25, 2019: <http://www.powerchemical.net/silicone_resin/silicone_resin_MQ.html>, (2017), 2 pgs.
"U.S. Appl. No. 15/042,557, Response filed Oct. 11, 2019 to Final Office Action dated Aug. 13, 2019", 11 pgs.
"U.S. Appl. No. 15/042,519, Response filed Oct. 11, 2019 to Non Final Office Action dated Jul. 11, 2019", 11 pgs.
"Chinese Application Serial No. 201680010426.2, Office Action dated Sep. 20, 2019", w/ English Translation, 9 pgs.
"Brazilian Application Serial No. BR112017015158-8, Office Action dated Oct. 15, 2019", w/ English Translation, 5 pgs.
"U.S. Appl. No. 15/042,557, Advisory Action dated Oct. 24, 2019", 5 pgs.
"Chinese Application Serial No. 201680010404.6, Office Action dated Oct. 25, 2019", w/ English Translation, 12 pgs.
"Chinese Application Serial No. 201680010557.0, Office Action dated Oct. 25, 2019", w/ English Translation, 13 pgs.
"Chinese Application Serial. No. 201680010405.0, Office Action dated Oct. 25, 2019", w/ English Translation, 14 pgs.
"U.S. Appl. No. 16/022,163, Notice of Allowance dated Nov. 14, 2019", 7 pgs.
"Chinese Application Serial No. 201680010560.2, Office Action dated Oct. 20, 2019", w/ English Translation, 15 pgs.
"Mexican Application Serial No. MX/a/2017/010512, Office Action dated Nov. 6, 2019", w/o English Translation, 6 pgs.
"Chinese Application Serial No. 201680010427.7, Office Action dated Dec. 24, 2019", w/ English translation, 10 pgs.
"Mexican Application Serial No. MX/a/20171010609, Response filed Nov. 1, 2019 to Office Action dated Aug. 29, 2019", w/ English Claims, 16 pgs.
"Chinese Application Serial No. 201680010426.2, Response filed Nov. 18, 2019 to Office Action dated Sep. 20, 2019", w/ English Claims, 7 pgs.
"Mexican Application Serial No. MX/a/2017/010512, Response filed Dec. 9, 2019 to Office Action dated Nov. 6, 2019", w/ English Claims, 13 pgs.
International Search Report and Written Opinion, PCT/US2016/017716, dated May 3, 2016.
Mark Fraser: "Silicones in Personal Care", Apr. 2004 (Apr. 5, 2004), XP055264504, Retrieved from the Internet: URL:http://skat.ihmc.us/rid=1099885933317_1921716679_1825/Silicones.pdf [retrieved on Apr. 12, 2016] slide 23: Skin Care and Color cosmetics: Fim Former/Transfer Resistance.
L "Belsil ADM 8301 E—Amino-Functional Silicone", Mar. 12, 2012 (Mar. 12, 2012), XP055160814, Retrieved from the Internet:URL:http://www.brenntagspecialties.com/en/downloads/Products/Personalcare/Wacker Silicones/Bel si 1 ADM 8301 E TDS.pdf [retrieved on Jan. 9, 2015].
"Wacker HC 303", Nov. 6, 2014 (Nov. 6, 2014), XP055264646, Retrieved from the Internet: URL:http://sdb.wacker.com/pf/e/result/report.jsp?P_LANGU=D&P_SYS=2&P_SSN=4950&PREP=00O000O000O00O000O04&P_Res=6209&P_SPEC=R [retrieved on Apr. 12, 2016].
Berthiaume M D: "Effects of silicone pretreatment on oxidative hair damage", Journal of the Society Cosmetic Chemists, Society of Cosmetic Chemists, US, vol. 46, No. 5, Sep. 1, 1995 (Sep. 1, 1995). pp. 231-245, XP002O92O29. ISSN: 0037-9832 Color Protection of Direct Dyes; p. 240.
"U.S. Appl. No. 15/042,519, Notice of Allowability dated Mar. 11, 2020", 2 pgs.
"U.S. Appl. No. 15/042,519, Notice of Allowability dated Apr. 21, 2020", 2 pgs.
"U.S. Appl. No. 16/022,163, 312 Amendment filed Mar. 16, 2020", 4 pgs.
"U.S. Appl. No. 16/022,163, Notice of Allowability dated Apr. 13, 2020", 2 pgs.
"U.S. Appl. No. 16/022,163, PTO Response to Rule 312 Communication dated Mar. 20, 2020", 2 pgs.

(56) References Cited

OTHER PUBLICATIONS

"Chinese Application Serial No. 201680010426.2, Office Action dated Feb. 6, 2020", W/ English Translation, 15 pgs.

* cited by examiner

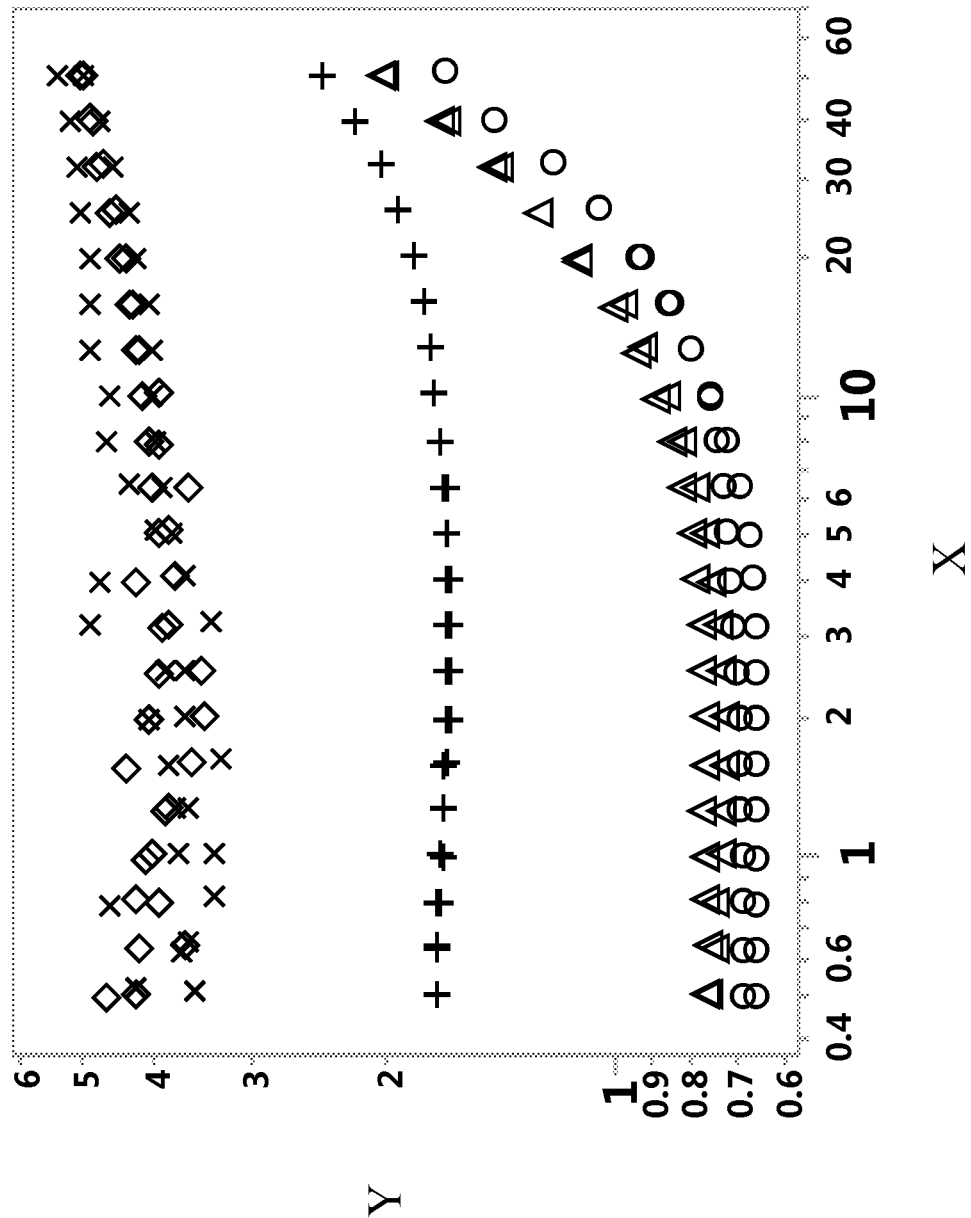

COMPOSITION FOR PROVIDING A FILM ON KERATIN FIBRES

FIELD OF THE INVENTION

The present invention relates to the field of cosmetics, particularly hair cosmetics, and relates to compositions for providing a film on keratin fibres.

BACKGROUND OF THE INVENTION

Semi-permanent treatments to human keratin fibres are well known in the art. Of particular note are semi-permanent treatments that alter the colour appearance of the hair or provide other coloured or reflective properties via the use of glitter or particles. For example, direct dyes colour the hair in a semi-permanent fashion by adhering coloured molecules to the keratin fibres. The dye can be later washed out. Hair chalks are powder-based or powdery products—typically provided in a blusher-style 'compact' or in pen format—that enable the user to apply pigments and/or coloured particles to the hair.

A drawback of the known technology in this area is low adherence of the pigment or coloured material to the keratin fibres—it is a significant consumer concern that such products can make your clothes and/or bathroom dirty and/or stained. Furthermore, such pigment or coloured material can migrate to the skin on your neck, shoulders and face and cause unsightly marks. Moreover, consumers wish to be able to apply. Chalk products typically provide a matt look, which may not be desired by all consumers and would not provide a vibrant, shiny look where the consumer desires this.

Thus there is a need for compositions and methods that provide more durable means to adhere pigments and/or coloured/shiny material to keratin fibres. In particular, there is a need for providing improved deposition of these particles. Furthermore, there is a need for providing a composition that is able to deposit a wide variety of particles—whether pigments, glitter or other coloured material. In addition, there is a need for such a composition that can be easily applied and distributed over the hair—for example does not result in clumping of the composition, or any kind of gluey-ness or gunky-ness of any kind on the head of hair. Indeed, there is a need for a more natural look to be provided by such means.

Teboul WO2014/001391A1, which published on 3 Jan. 2014 relates to a "process for dyeing keratin fibres, in particular the hair, which consists in applying to the keratin fibres: —at least one coat of at least a first composition (i) comprising at least one hydrophobic film-forming polymer, at least one volatile solvent and at least one pigment, and then, after drying the said coat, at least a second coat of at least a second composition (ii) comprising at least one hydrophobic film-forming polymer, at least one volatile solvent and at least one pigment . . . ". Teboul does not disclose an aminosilicone polymer comprising an amino side chain. Maillefer et al in EP2090295A1, which published on 19 Aug. 2009, mentions pigments in § 127, but in the context of a "method and composition for improving the drying time of hair". For example, there is no teaching in Maillefer et al on deposition enhancers. Calaco et al in WO2013/085577A2, which published on 13 Jun. 2013, mentions compositions and methods are disclosed for imparting a long-wearing color to keratin fibers. However, Calaco et al also does not teach deposition enhancement.

None of the prior art teach or provide solutions that fulfil all the consumers' needs.

SUMMARY OF THE INVENTION

A composition for providing a film on keratin fibres is provided and comprises:
(a) a film-forming aminosilicone polymer, wherein the aminosilicone polymer comprises amino sidechains, and wherein the aminosilicone polymer has a weight average molecular weight of from 10,000 Dalton to 60,000 Dalton;
(b) a silicone resin wherein the silicone resin is a MQ resin;
(c) a thickening system comprising:
a deposition enhancer, wherein the deposition enhancer is a hydrophilic and non-ionic polymer, and wherein the deposition enhancer has a weight average molecular weight of from 700,000 Dalton to 3,000,000 Dalton;
a thickening polymer, wherein the thickening polymer has a weight average molecular weight of at least 10,000 Dalton, and wherein the thickening polymer is a cationic thickening polymer or is a non-ionic thickening polymer; and
(d) a solvent.

A method for providing a film comprising pigment or coloured material onto keratin fibres is provided and comprises: applying the composition according to the present invention onto keratin fibres and allowing the keratin fibres to dry or drying them.

A third aspect relates to a kit comprising:
the composition according to the present invention;
optionally a formulation comprising pigment and/or coloured material; and
an applicator.

BRIEF DESCRIPTION OF THE DRAWINGS

FIG. 1: Rheological measurements of compositions according to the present invention. X=strain (%) and Y=tangent delta.

DETAILED DESCRIPTION OF THE INVENTION

Definitions and General

In this document, including in all embodiments of all aspects of the present invention, the following definitions apply unless specifically stated otherwise. All percentages are by weight (w/w) of the total composition. All ratios are weight ratios. "wt %" means percentage by weight. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR®

International. Herein "min" means "minute" or "minutes". Herein "mol" means mole. Herein "g" following a number means "gram" or "grams". All amounts as they pertain to listed ingredients are based on the active level ('solids') and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

"Viscosity" is measured at 23° C. using a HAAKE Rotation Viscometer VT 550 with cooling/heating vessel and sensor systems according to DIN 53019 at a shear rate of 12.9 $s^{-1}$.

"Water-soluble" refers to any material that is sufficiently soluble in water to form a clear solution to the naked eye at a concentration of 0.1% by weight of the material in water at 23° C. The term "water-insoluble" refers to any material that is not "water-soluble".

"Dry" or "substantially dry" means comprising less than 5%, less than 3% or, less than 2%, less than 1%, or about 0% of any compound or composition being in liquid form when measured at 23° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Substantially free from" or "substantially free of" means less than about 1%, or less than 0.8%, or less than 0.5%, or less than 0.3%, or about 0%, by total weight of the composition or formulation.

The term "molecular weight" or "M.Wt." as used herein refers to the weight average molecular weight unless otherwise stated. The weight average molecular weight may be measured by gel permeation chromatography.

"Volatile" means materials that are liquid under ambient conditions and which have a measurable vapour pressure at 25° C. These materials have a vapour pressure greater than 1.3 Pa, or from 26.7 Pa to 5 kPa, and a standard boiling point less than 250° C., or less than 235° C., or less than 150° C. "Standard boiling point" is as defined by the International Union of Pure and Applied Chemistry (IUPAC).

"Hair" means mammalian keratin fibres including scalp hair, facial hair and body hair. It includes such hair still being attached to a living subject and also hair that has been removed therefrom such as hair swatches and hair on a doll/mannequin. "Hair" may mean human hair only. "Hair shaft" or "hair fibre" means an individual hair strand and may be used interchangeably with the term "hair."

"Proximal to the scalp" means that portion of an extended, or substantially straightened, hair shaft that is closer in distance to the scalp than to the end of the hair. Thus, 50% of the hair fibre length would be considered proximal to the scalp, and 50% of the hair fibre would be distal to the scalp. "z cm proximal to the scalp" means a distance "z" along the hair, with one endpoint being on or directly adjacent to the scalp, and the second endpoint being measured "z" centimetres along the length of the extended or substantially straightened hair.

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. "Derivatives thereof" may mean the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is, for example, a first composition and a separately packaged second composition and optionally application instructions.

"Hairstyling polymer" means a hair-fixing polymer which forms a film on a surface i.e. a film-forming polymer. 'Hairstyling polymer' and 'film-forming polymer' are used interchangeably in the art. In the context of hair science, this surface is the surface of individual hair fibres or a plurality thereof. The hairstyling polymer causes the hair fibres to be glued together to build welds, which are effectively cross-links that provide the hold benefit. In concert, these welds form a 'hairnet' to provide hair hold and volume benefits to the consumer. When the net of welds is effectively formed, the hold and volume benefits can last all day and offer good resistance to environmental humidity.

Theory Behind and Advantages of the Present Invention

The inventors provide herein a composition for providing a film on keratin fibres, more particularly a composition for providing a coloured film on keratin fibres. Indeed, the combination of film-forming aminosilicone polymer, silicone resin, solvent and selected thickening system results in a film on keratin fibres, particularly human head hair, that is sufficiently durable that it does not quickly rub off whilst on the keratin fibres, for example on the hands, clothes etc of the consumer, nor does it provide bad hair feel, such as lumpiness, nor abrasiveness, nor weigh down the hair reducing the head of hair volume, nor unsightly globules.

Indeed, the film-forming aminosilicone polymer and silicone resin enable the forming of a very thin, dry film, which tightly binds any coloured material and/or pigment onto the hair fibres in a durable fashion. The aminosilicone polymer and silicone resin provides an excellent film via a dehydration mechanism.

The selected thickening system can help to prevent dripping of the composition by inhibiting capillary action, which would otherwise quickly draw the composition down the fibres and onto the floor and/or clothes of the user. Nevertheless, the thickening system, particularly the combination of thickening polymer and deposition enhancer, provide a non-dripping composition that adheres well to keratin fibres without generating a sticky feel. Moreover, the thickening system does not detract from the ability of the film-forming aminosilicone polymer and silicone resin to provide the thin, dry film.

In particular, the present invention overcomes the drawbacks demonstrated by previous developments in this area in that it is able to provide subtle hair effects that can be employed by a much wider variety of end-consumers in a wider variety of life contexts. In other words, the effects provided by the present invention are not limited to highly vibrant and dazzling hair effects that are often used prior to visiting a disco or nightclub, but also provides chic hair looks that are acceptable in a business context and also not too overpowering for everyday hair looks.

Indeed, the selected combination of features—the combination of film-forming aminosilicone polymer, silicone resin, solvent and selected thickening system—provides an excellent support system for coloured material and/or pigments, which can provide the desired effects to the hair, such as glitteriness, colour, shininess etc. Said coloured material and/or pigments may be provided separately from the composition chassis such that the consumer and/or stylist can select the exact the exact type of pigment and/or coloured material desired.

Composition of the First Aspect

The composition as set out herein above is for providing a film on keratin fibres. The composition may be for providing a film comprising pigment or coloured material on keratin fibres. The film may be a durable film.

The composition may be substantially free of compounds causing precipitation of any component of the composition when the composition is in aqueous solution at pH 5 and at 23° C. When the composition typically comprises a film-forming aminosilicone polymer, a MQ resin, a thickening system comprising a deposition enhancer and a thickening polymer, and a solvent, the pH of the composition may be between 4 and 6, preferably between 4.5 and 5.5. Examples of compounds causing precipitation of any component of the composition when the composition is in aqueous solution at pH 5 and at 23° C. may be a basic solvent, or ionic compounds or compounds that are cationic from pH 4 to 6, preferably from pH 5 to 6 or compounds having a relative ionic strength.

Indeed, precipitation of any component of the present composition would have negative side effects on the efficacy of the present invention—particularly in terms of hair feel. Indeed, with the exclusion of the pigment and/or coloured material that is herein intended to be immobilised on hair, other residues on hair are not accepted by the consumer. For example, precipitation of the film-forming aminosilicone polymer and/or silicone resin would detract from their ability to form a film on the hair fibres and would form residues on hair. The composition may be substantially free of any further ionic compounds. The composition may be substantially free of any compounds that are cationic at pH 4.0 to 5.0.

Aminosilicone & Silicone Resin

The composition comprises a film-forming aminosilicone polymer, wherein the aminosilicone polymer comprises amino side chains, and wherein the aminosilicone polymer has a weight average molecular weight of from 10,000 Dalton to 60,000 Dalton. "Sidechain" (aka "side chain") in the context of a silicone refers to a group being not part of the silicone backbone nor only present on at least one terminus of the silicone backbone. "Terminal aminosilicone" as defined herein means silicone comprising one or more amino groups at one or both ends of the silicone backbone Aminosilicone polymers having amino side chains are sometimes referred to as silicone compounds comprising pendant amino groups. The aminosilicone polymer may be not a terminal aminosilicone. The composition may be substantially free of silicones having terminal amino groups.

The aminosilicone polymer is a film-forming aminosilicone polymer. The aminosilicone polymer may be a polydimethylsiloxane having graft amino groups.

The aminosilicone polymer may have a weight average molecular weight of from 15,000 Dalton to 50,000 Dalton, or from 20,000 Dalton to 40,000 Dalton.

The aminosilicone polymer may be a polydimethylsiloxane polymer having pendent (graft) amino groups. The aminosilicone polymer may conform to the formula:

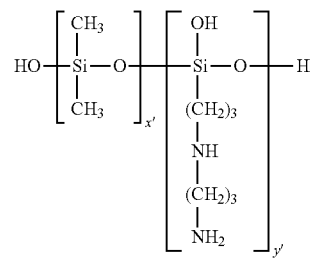

. . . in which x' and y' are integers such that the weight average molecular weight is between 10,000 Dalton and 60,000 Dalton. The endcaps may be methoxy rather than hydroxyl as pictured in the above formula.

The aminosilicone polymer may be a polydimethylsiloxane polymer having a sidechain with from 3 to 8 carbon atoms. The sidechain may comprise carbon, hydrogen and nitrogen atoms. The sidechain may consist of carbon, hydrogen and nitrogen atoms. The aminosilicone polymer may be a polydimethylsiloxane polymer having an aminoethyl aminopropyl sidechain.

The aminosilicone polymer may conform to the formula:

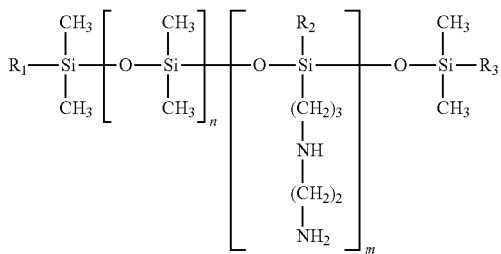

... in which n and m are integers such that the weight average molecular weight is between 10,000 Dalton and 60,000 Dalton, $R_1$ and $R_3$ are independently selected from —OH or —OCH$_3$; $R_2$ is H or a $C_1$ to $C_3$ alkyl, or methyl or H, preferably methyl. "n" may be on average from 1 to 50, or from 5 to 20, or from 6 to 10, or from 8 to 9, and "m" may be on average from 120 to 300, or from 150 to 200. "n" may be on average from 5 to 8, "m" may be on average from 150 to 180, $R_1$ and $R_3$ may be both methyl, and $R_3$ may be —OCH$_3$.

The aminosilicone polymer may have an amine number of from 0.1 meq/g to 3 meq/g, or from 0.7 meq/g to 2.5 meq/g, or from 0.6 meq/g to 1 meq/g.

Suitable example aminosilicone polymers can be found in the following patent documents, which are incorporated herein by reference: Decoster U.S. Pat. No. 6,451,747B1 col. 17, 1.4-27; Hughes U.S. Pat. No. 5,567,428 col. 13, 1.40-56; Gawtrey et al US2004/0010863A1, § 0016 to § 0039; Mahr et al US2006/0041026A1.

The composition may comprise from 1% to 15%, or from 1.5% to 5% of an aminosilicone polymer. The viscosity of the aminosilicone polymer may be from 10 to 100,000 mPa·s, or from 100 to 10,000 mPa·s.

The composition comprises a silicone resin. Silicone resins are known in the art. The silicone resin may be a film-forming polymer. The silicone resin is an MQ resin. "M" stands for Me$_3$SiO and "Q" stands for SiO$_4$. The MQ resin may have an M:Q molar ratio of from 0.5:1.0 to 1.5:1.0. The weight average molecular weight of the resin may be from 1000 Daltons to 10,000 Daltons. The MQ resin may contain at least 80 mol. %, or at least 95 mol. %, of units of the general formulae below:

in which $R^7$ is $C_{1-40}$ alkyl, H, —OR or —OH radicals. The ratio of the units of the general formulae may be from 0.5 to 2.0, or from 0.5 to 1.5. The not more than 3% by weight, or not more than 2.5% by weight, of the radicals $R^7$ may be —OR and —OH.

The remaining units of the MQ silicone resin may be units of the following general formulae:

in which $R^7$ is $C_{1-40}$ alkyl, H, —OR or —OH radicals.

$R^7$ may be $C_{1-40}$ alkyl that is optionally halogen-substituted, linear, cyclic, branched, aromatic, saturated or unsaturated. $R^7$ may be an alkyl group having $C_{1-6}$ carbon atoms, or a phenyl radical. The halogen substituents may be selected from fluorine and chlorine. $R^7$ may be selected from methyl, ethyl, phenyl and H. The composition may comprise from 0.1% to 10%, or from 1% to 5%, or from 2% to 4% of a MQ resin.

MQ resins are available from Wacker-Chemie AG, D-81737 München, Germany. For example, MQ-RESIN POWDER 803 TF is a co-hydrolysis product of tetraalkoxy silane (Q unit) and trimethyl-ethoxy silane (M unit) and can be seen as a three dimensional network of polysilicic acid units which are endblocked with trimethylsilyl groups. Some residual ethoxy and hydroxy functions are present. MQ resins are also available from Dow Corning. For example, Dow Corning® MQ-1640 Flake Resin is a combination of MQ and T propyl silicone resin and has the INCI name: Trimethylsiloxy silicate (and) Polypropyl silsesquioxane.

The composition may comprise an ether of a water-soluble polyhydric alcohol. The ether of a water-soluble polyhydric alcohol has the advantage that it is able to prevent the aminosilicone and the silicone resin from forming a complex. The ether of a water-soluble polyhydric alcohol may be a non-polymeric, amphiphilic compound. Indeed, the aminosilicone comprises amino side chains, which lend hydrophilic character to the aminosilicone, and the silicone resin typically is hydrophobic in nature. Thus where the ether of a water-soluble polyhydric alcohol has amphiphilic chemistry it can interact with both the aminosilicone and the silicone resin and keep them from clumping, and also from precipitating. The composition may comprise ether of a water-soluble polyhydric alcohol, wherein the ether of a water-soluble polyhydric alcohol is selected from the group consisting of diethyleneglycol monobutylether, ethylene glycol monohexyl ether, and a mixture of diethyleneglycol monobutylether and ethylene glycol monohexyl ether. The composition may comprise from 0.01% to 20%, or from 0.1% to 10%, or from 0.5% to 5%, or from 1.0% to 5%, or from 2% to 5% ether of a water-soluble polyhydric alcohol.

A suitable product for use in the present invention is available under the trade mark Wacker®/BELSIL ADM 8301 E by the company Wacker-Chemie AG, D-81737 München, Germany. This product contains from 10% to 20% of poly[3-((2-aminoethyl)amino)propyl]methyl(dimethyl)siloxane, hydroxyterminated, which is an aminosilicone. It also contains from 0.1% to 0.2% octamethylcyclotetrasiloxane and from 1% to 5% of an MQ silicone resin. The product also contains from 1% to 3% ethylene glycol monohexyl ether and from 5% to 10% diethyleneglycol monobutylether. Said product is described in US2006/0041026A1 which is incorporated herein by reference. A similar product is Wacker® HC303 also from Wacker-Chemie AG.

Thickening System

The composition comprises a thickening system. The thickening system comprises a deposition enhancer and a thickening polymer. The composition may comprise from 0.5% to 2% of a thickening system.

The thickening system comprises a deposition enhancer. The deposition enhancer is a hydrophilic and non-ionic polymer, and wherein the deposition enhancer has a weight average molecular weight of from 700,000 Dalton to 3,000,000 Dalton. The deposition enhancer is useful for aiding the deposition of the aminosilicone and silicone resin as well as any pigment and/or coloured material on to the hair fibre. In particular, the deposition enhancer has the advantage that more aminosilicone and silicone resin as well as any pigment and/or coloured material stays on the hair fibre rather than dripping or sliding off the hair fibre. Indeed, in view of the physical structure of a head of hair i.e. a plurality of fibres that are close proximity to one another, capillary action plays a role with regards to fluids on hair. Hence, the deposition enhancer is useful for preventing the capillary action from stripping the aminosilicone, silicone resin and any pigment and/or coloured material from the hair.

The composition may comprise from 0.01% to 5% of a deposition enhancer. The composition may comprise from 0.05% to 4%, or from 0.075% to 3.5%, or from 0.1% to 3%, or from 0.1% to 2%, or from 0.15% to 1% of a deposition enhancer.

The deposition enhancer may conform to the formula $H(OCH_2CH_2)_nOH$ wherein n has an average value of from 20,000 to 50,000. The deposition enhancer may conform to the formula $H(OCH_2CH_2)_nOH$ wherein n has an average value of from 40,000 to 50,000. The composition may comprise from 0.01% to 5% of a deposition enhancer. The composition may comprise from 0.05% to 4%, or from 0.075% to 3.5%, or from 0.1% to 3%, or from 0.1% to 2%, or from 0.15% to 1% of a deposition enhancer, wherein the deposition enhancer conforms to the formula $H(OCH_2CH_2)_nOH$ wherein n has an average value of from 40,000 to 50,000.

The deposition enhancer may have a weight average molecular weight of from 1,000,000 Dalton to 2,500,000 Dalton.

Useful deposition enhancers are available from Dow under their POLYOX brand. In particular, POLYOX WSR N-60K is PEG-45M i.e. formula $H(OCH_2CH_2)_nOH$ wherein n is an integer and where n has an average value of 45,000. PEG-45M has a weight average molecular weight of 2,000,000 Dalton. Also useful is POLYOX WSR N-12K, which is PEG-23M i.e. formula $H(OCH_2CH_2)_nOH$ wherein n is an integer where n has an average value of 23,000. PEG-23M has a weight average molecular weight of 1,000,000 Dalton. Also useful is POLYOX WSR-1105, which has a weight average molecular weight of 900,000 Dalton.

The thickening system comprises a thickening polymer. The thickening polymer has a weight average molecular weight of at least 10,000 Dalton. The thickening polymer is a cationic thickening polymer or is a non-ionic thickening polymer. The composition may comprise from 0.01% to 5% of a thickening polymer. The composition may comprise from 0.1%, or from 0.2%, or from 0.3%, or from 0.4, or from 0.5%, or from 0.6%, or from 0.7%, or from 0.8%, or from 0.9% to 5%, or to 4.5%, or to 4%, or to 3.5%, or to 3%, or to 2.5%, or to 2%, or to 1.5% of a thickening polymer. The thickening polymer may be a non-ionic thickening polymer.

The thickening polymer may be a polysaccharide. The thickening polymer may be a polysaccharide and the polysaccharide may be selected from the group consisting of hydroxyethylcellulose, hydroxypropylcellulose, starch compounds, xanthan gum, carrageenans, and mixtures thereof. The thickening polymer may be a heteropolysaccharide. The total polysaccharide content present in the composition may be from 0.2% to 5%, or from 0.5% to 4%. Suitable polysaccharides and heteropolysaccharides may include starches and derivatives thereof, e.g. mono- or di-esters with phosphoric acid, cellulose types and their derivatives, xanthan gums, carrageenans. Heteropolysaccharides may include xanthan gum such as Keltrol® from Kelco, and Natrosol® 250 HHR from Herkules. The viscosity-increasing agent may be a starch compound. The viscosity-increasing agent may be a hydroxypropyl starch phosphate. An example of a hydroxypropyl starch phosphate may be Structure® XL from Akzo Nobel. The thickening polymer may be a hydroxyethyl cellulose. The hydroxethyl cellulose may conform to the formula below:

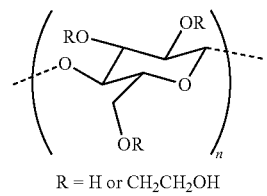

$R = H$ or $CH_2CH_2OH$

A suitable hydroxethyl cellulose is Cellosize™ HEC QP 4400 from Dow.

The thickening polymer may be a cationic thickening polymer. The thickening polymer may comprise a hydrocarbon backbone substituted with an amino-group containing sidechain. The thickening polymer may be a cationic thickening polymer comprising a quaternary amine group, alternatively a quaternary ammonium group. The thickening polymer may have the below structure:

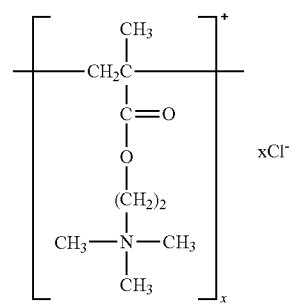

The thickening polymer may be a Polyquaternium-37. Polyquaternium-37 is a poly(2-methacryloxyethyltrimethylammonium chloride). Polyquaternium-37 is available from BASF via the product Salcare® SC 96 FROM BASF, which has the INCI name: Polyquaternium-37 (and) Propylene Glycol Dicaprate Dicaprylate (and) PPG-1 Trideceth-6. Polyquaternium-37. Polyquaternium-37 is also available as: Syntran PC 5320 (Interpolymer Corporation); Ultragel® 300 from Cognis GmbH; OriStar PQ37 from Orient Stars LLC; Synthalen CN from 3V Group; Synthalen CR from 3V Group; Synthalen CU from 3V Group; Cosmedia® Triple C from Cognis GmbH, which has the INCI: Polyquaternium-37, Dicaprylyl Carbonate, Lauryl Glucoside.

Where the composition comprises a thickening polymer being a cationic thickening polymer comprising a quaternary amine group, alternatively a quaternary ammonium group, the composition may have a pH in the range pH 3 to pH 5, or from pH 3.5 to pH 4.5. The pH range can be useful in ensuring that the thickening polymer does not act as a nucleophile.

Pigments

The composition may comprise one or more pigments. The one or more pigments may be one or more coloured pigments which impart colour effects to the product mass or to the hair. Alternatively, the one or more pigments may be lustre effect pigments which impart desirable and aesthetically pleasing lustre effects to the composition or to the keratin fibres. The colour or lustre effects on the hair may be preferably temporary, i.e. they last until the next hair wash and can be removed again by washing the hair with customary shampoos.

The composition may comprise one or more pigments having a $D_{50}$ particle diameter of from 5 micron to 60 micron. Particle diameter is represented by $D_{50}$, which is the median diameter by volume. $D_{50}$ is measured with a Malvern Mastersizer 2000, which is a laser diffraction particle sizer and it is measured according to ISO 13320: 2009(en) with Hydro 2000G or Hydro 2000S where the dispersant is water or ethanol. Detection range is from 0.02 micron to 2000 micron. $D_{50}$ is expressed as $x_{50}$ in ISO 13320:2009(en). Laser diffraction measures particle size distributions by measuring the angular variation in intensity of light scattered as a laser beam passes through a dispersed particulate sample analyser and the particle size is reported as a volume equivalent sphere diameter. A discussion of calculating $D_{50}$ is provided in Barber et al, Pharmaceutical Development and Technology, 3(2), 153-161 (1998), which is incorporated herein by reference.

The composition may comprise one or more pigments having a $D_{50}$ particle diameter of from 10 micron to 40 micron. The one or more pigments may be present in the composition in an undissolved form. The composition may comprise from 0.01% to 25%, or from 0.1% to 20% of one or more pigments, or from 1% to 15%, or from 4% to 10% of the one or more pigments.

The one or more pigments may be one or more colorants which are virtually insoluble in the composition, and may be inorganic or organic. Inorganic-organic mixed pigments may be also possible. The composition may comprise one or more inorganic pigments. The advantage of the one or more inorganic pigments is their excellent resistance to light, weather and temperature. The one or more inorganic pigment may be of natural origin, and are, for example, derived from material selected from the group consisting of chalk, ochre, umber, green earth, burnt sienna, and graphite.

The one or more pigment may be one or more white pigments, such as, for example, titanium dioxide or zinc oxide, or may be one or more black pigments, such as, for example, iron oxide black, or may be one or more coloured pigments, such as, for example, ultramarine or iron oxide red, one or more lustre pigments, one or more metal effect pigments, one or more pearlescent pigments, and one or more fluorescent or one or more phosphorescent pigments.

The one or more pigment may be one or more coloured, non-white pigments. The one or more pigments may be selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze pigments). The one or more pigments may be selected from the group consisting of are titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), and combinations thereof.

The one or more pigments may be one or more pearlescent and coloured pigments based on mica which are coated with a metal oxide or a metal oxychloride, such as titanium dioxide or bismuth oxychloride, and optionally further colour-imparting substances, such as iron oxides, Prussian blue, ultramarine, and carmine. The colour exhibited by the one or more pigments can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for colour travel pigments that display colour shifting effects depending on the viewing angle and are based on either natural mica, silica ($SiO_2$) or calcium aluminium borosilicate flakes, coated with varying layers of titanium dioxide ($TiO_2$).

Pigments from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and $TiO_2$) having a $D_{50}$ particle diameter of 5 to 25 micron and also KTZ® CELESTIAL LUSTER (mica and $TiO_2$, 10 to 60 micron) as well as KTZ® CLASSIC WHITE (mica and $TiO_2$, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection colour and is composed of platelets of synthetic fluorphlogopite and coated with titanium dioxide and iron oxides. Also useful is Duocrome® RV 524C from BASF, which provides a two colour look via a lustrous red powder with a violet reflection powder due to its composition of mica, titanium dioxide and carmine.

The one or more pigments may be one or more organic pigments. The one or more organic pigments may be selected from the group consisting of natural pigments sepia, gamboge, bone charcoal, Cassel brown, indigo, chlorophyll and other plant pigments.

The one or more organic pigments may be one or more synthetic organic pigments. The one or more synthetic organic pigments may be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof.

The one or more pigments may be selected from the group consisting of iron oxide, titanium dioxide, mica, borosilicate, and combinations thereof. The one or more pigments may comprise one or more iron oxide ($Fe_2O_3$) pigments. The one or more pigments may comprise a combination of mica and titanium dioxide.

Coloured Material

The composition may comprise one or more coloured material. The one or more coloured materials may be particulate in form. The one or more coloured materials may be selected from the group consisting of coloured fibres, coloured beads, coloured particles such as nano-particles, coloured polymers comprising covalently attached dyes, liquid crystals, particles having diffraction properties, UV absorber and photoprotective substances, pressure- or light-sensitive pigments, and combinations thereof.

The one or more coloured materials may be capable of changing colour via a mechanism selected from the group consisting of thermochromism, photochromism, hydrochromism, magnetochromism, electrochromism, piezochromism, chemichromism, mechano-optics. Suitable materials may include 3D Magnetic Pigments, Glow Dust, Fluorescent Pigments, Thermo Dust, Chameleon Pigments and other colour changing materials from Solar Color Dust (http://solarcolordust.com/).

The composition may comprise one or more photoprotective substances. The composition may comprise from 0.01 to 10%, or from 0.1 to 5%, or from 0.2 to 2% of the one or more photoprotective substances. Useful photoprotective substances are specified in EP1084696A1 from § 0036 to § 0053, which is incorporated herein by reference. The one or more photoprotective substances may be selected from the group consisting of 2-ethylhexyl 4-methoxy-cinnamate, methyl methoxycinnamate, 2-hydroxy-4-methoxybenzophenone-5-sulfonic acid, polyethoxylated p-aminobenzoates, di-butyl-hydroxytoluene (BHT), and mixtures thereof.

The composition may comprise from 0.01% to 10%, or from 0.05% to 5% of one or more particulate substances. The one or more particulate substances may be substances which are solid at room temperature (23° C.) and may be in the form of particles. The one or more particulate substances may be selected from the group consisting of silica, silicates, aluminates, clay earths, mica, and insoluble salts. The one or more particulate substances may be selected from the group consisting of insoluble inorganic metal salts, metal oxides, minerals and insoluble polymer particles. The one or more particulate substances may be titanium dioxide.

The one or more particulate substances may be present in the composition in undissolved, or stably dispersed form, and, following application to the hair and evaporation of the solvent, can deposit on the hair in solid form.

The one or more particulate substances may be selected from the group consisting of silica (silica gel, silicon dioxide) and metal salts, in particular inorganic metal salts. The one or more particulate substances may be silica. The one or more particulate substances may be selected from the group consisting of metal salts such as alkali metal or alkaline earth metal halides, e.g. sodium chloride or potassium chloride; alkali metal or alkaline earth metal sulfates, such as sodium sulfate or magnesium sulfate.

Solvent

The composition comprises a solvent. The solvent may be a cosmetically acceptable carrier. The composition may comprise water. Water may be useful because it provides a hydrophilic phase, which the hydrophilic portions of the components can interact with. Water may be also useful because it can provide a fluid phase meaning that the composition can be in liquid form and therefore can be easily mixed with other fluids. The composition may comprise from 40% to 90%, or 50% to 85%, or from 55% to 80% water. The solvent may comprise water and wherein the composition may comprise from 50% to 85% of water.

The composition may be an aqueous, alcoholic or aqueous-alcoholic composition comprising at least 10% water. The composition may comprise further water-miscible or water-soluble solvents. The composition may comprise at least one $C_1$-$C_5$ alkyl monohydric alcohol, or at least one $C_2$-$C_3$ alkyl alcohols. The composition may comprise ethanol and/or isopropanol. The composition may comprise a co-solvent. The co-solvent may be a cosmetically acceptable organic solvent or a mixture of solvents with a boiling point below 400° C. The composition may comprise from 0.1% to 15% co-solvent, or from 1% to 10% co-solvent. The co-solvent may be selected from the group consisting of unbranched or branched hydrocarbons, such as pentane, hexane, isopentane; cyclic hydrocarbons, such as cyclopentane and cyclohexane. The composition may comprise glycerol, ethylene glycol, propylene glycol, or a mixture thereof.

Anti-freeze Agent

The composition may comprise from 0.5% to 30% of a volatile alcohol, wherein the volatile alcohol may have from 1 to 8 carbon atoms and may be miscible in water. The volatile alcohol may act as an anti-freeze agent (or a first anti-freeze agent). An anti-freeze agent has the advantage that it lowers the freezing point of a composition and consequently prevents the composition from freezing, which can prevent any unwanted side effects of freezing and/or subsequent thawing.

The composition may comprise from 0.5% to 3%, or from 0.75% to 2.5%, or from 1% to 2% of a volatile alcohol, wherein the volatile alcohol may have from 1 to 8 carbon atoms and may be miscible in water. The volatile alcohol may be a monohydric alkyl alcohol having from 1 to 4 carbon atoms. The volatile alcohol may be selected from the group consisting of alkoxylated alcohols having a maximum of 8 carbon atoms, ethanol, propanol, isopropanol, and mixtures thereof. The volatile alcohol may be selected from the group consisting of isopropanol, $CH_3CH_2OCH_2CH_2OCH_2CH_2OH$, $CH_3OCH_2CH(CH_3)OCH_2CH(CH_3)OH$, $CH_3CH(OH)CH_2OCH_2CH(CH_3)OCH_3$, $CH_3CH_2OH$, and mixtures thereof. Miscibility in water can be useful in view of the advantages of using water as a solvent. Indeed, the solvent may be water and/or the majority of the solvent may be water. Since the present first aspect is "for providing a film on keratin fibres", the volatility of the alcohol can be chosen such that solvent and other non-film-forming compounds evaporate. A suitable product for providing the volatile alcohol can be Aquasolved Super from Firmenich.

The composition may comprise a first anti-freeze agent and a further anti-freeze agent. The further anti-freeze agent may modify the effects of the first anti-freeze agent, for example, by altering any negative effects of the first anti-freeze agent. The composition may comprise from 0.1% to 2%, or from 0.2% to 1% of a further anti-freeze agent. The further anti-freeze agent may be a surfactant, for example a non-ionic surfactant. The further anti-freeze agent may be a non-ionic surfactant having from 20 to 50 carbon atoms, or from 22 to 25 carbon atoms. The non-ionic surfactant may be an ether of a polyethylene glycol. The non-ionic surfactant may be a $C_{5-32}$ alkyl alcohol ether of a polyethylene glycol. The non-ionic surfactant may be a $C_{10-25}$ alkyl alcohol ether of a polyethylene glycol. Said polyethylene glycol may conform to the formula $H(OCH_2CH_2)_nOH$ wherein n is an integer from 1 to 20, or from 5 to 12. The non-ionic surfactant may be an ether of triglycerin, hexaglycerin, PPG-4, PPG-6, PEG-5, PEG-6, PEG-8, PEG-12, PEG-14, PEG-18, or PEG-20. A suitable non-ionic surfactant may be Tergitol™ 15-S-9 from Dow, which has the INCI name C11-15 Pareth-9 and may be the polyethylene glycol ether of a mixture of synthetic $C_{11-15}$ fatty alcohols with an average of 9 moles of ethylene oxide. Another suitable non-ionic surfactant may be trideceth-12.

Preservative

The composition may comprise at least one preservative and/or a mixture of preservatives. The preservative and/or mixture of preservatives may be active against gram negative bacteria, *Staphylococcus aureus* and *Candida albicans*. The composition may comprise 2-phenoxyethanol and/or phenylmethanol. The composition may comprise 2-phenoxyethanol. The composition may comprise from 0.01% to 5% of a preservative, or from 0.1% to 2%, or from 0.5% to 1.5% of a preservative. The preservative may be selected from the group consisting of benzyl alcohol, phenoxyethanol, and mixtures thereof. The composition may comprise at least one preservative; and wherein the preservative may be selected from the group consisting of benzyl alcohol and phenoxyethanol; or wherein the preservative may be a mixture of benzyl alcohol and phenoxyethanol.

The composition may be substantially free of esters of parahydroxybenzoic acid. Esters of parahydroxybenzoic acid are commonly known as parabens. Parabens are not preferred by some consumers.

The composition may be substantially free of isothiazolinone compounds. The composition may be substantially free of benzoate compounds. Benzoate compounds are not preferred in view of the potential for instability and/or precipitation of the composition. The composition may be substantially free of 1,3-bis(hydroxymethyl)-5,5-dimethylimidazolidine-2,4-dione.

Perfume

The composition may comprise one or more perfumes. The composition may comprise from 0.001% to 2% of the one or more perfumes. The one or more pigments and/or the one or more coloured materials may have perfumed coating. The one or more perfumes may also be provided via an encapsulated perfume i.e. a perfume provided inside a microcapsule.

The microcapsule features friction-triggered release technology i.e. the contents of the microcapsule may be released upon exposing the microcapsule friction. Said friction could be the action of sponging the composition according to the present invention onto the hair or combing the hair after the composition has been applied. The microcapsule may be a friable microcapsule. A friable microcapsule may be configured to release the core material when the outer shell is ruptured. The microcapsule may comprise a shell made from a synthetic polymeric material. The microcapsule may comprise a core material and a shell surrounding the core material, wherein the shell may comprise: a plurality of amine monomers selected from the group consisting of aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiobutyl aminoethyl methacrylates, diethylaminoethyl methacrylates, dimethylaminoethyl methacrylates, dipropylaminoethyl methacrylates, and mixtures thereof; and a plurality of multifunctional monomers or multifunctional oligomers. The shell may consist of a polyacrylate material, such as a polyacrylate random copolymer.

The microcapsule features moisture-triggered release technology i.e. the contents of the microcapsule may be released upon contact with moisture. The microcapsule may comprise cyclic oligosaccharides, or the microcapsule matrix or shell may be made from cyclic oligosaccharides. "Cyclic oligosaccharide" as used herein means a cyclic structure comprising six or more saccharide units. The cyclic oligosaccharides may have six, seven, or eight saccharide units or combinations thereof. It is common in the art to refer to six, seven and eight membered cyclic oligosaccharides as α, β, and γ, respectively. The cyclic oligosaccharides may be selected from the cyclodextrins: methyl-α-cyclodextrins, methyl-β-cyclodextrins, hydroxypropyl-α-cyclodextrins, hydroxypropyl-β-cyclodextrins, and mixtures thereof. The cyclodextrins may be in the form of particles. The cyclodextrins may also be spray-dried.

The one or more perfumes may be an animal fragrance or a plant fragrance. The animal fragrance may be selected from consisting of musk oil, civet, castoreum, ambergris, and mixtures thereof. The plant fragrance may be selected from consisting of nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, *eucalyptus* oil, *verbena* oil, *mimosa* extract, *narcissus* extract, carrot seed extract, jasmine extract, olibanum extract, rose extract, and mixtures thereof.

The perfume may be selected from the group consisting of acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, maj antol, mayol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox, and mixtures thereof.

pH

The pH of the composition may be from 3.0 to 11.0, or from 3.5 to 8.0, or from 3.5 to 5.5, or from 4.0 to 5.0. The pH may be useful in ensuring cosmetic compatibility and stability of the composition. For example, a too high or too low pH can cause components to precipitate, which could lead to undesirable residues on hair.

The composition may comprise a pH modifier and/or buffering agent. The amount of the pH modifier and/or buffering agent may be sufficiently effective to adjust the pH of the composition. Suitable pH modifiers and/or buffering agents for use herein may include, but are not limited to ammonia, alkanolamines such as monoethanolamine, diethanolamine, triethanolamine, monopropanolamine, dipropanolamine, tripropanolamine, 2-amino-2-methyl-1-propanol, and 2-amino-2-hydroxymethyl-1,3,-propanediol and guanidium salts, alkali metal and ammonium hydroxides and carbonates, preferably sodium hydroxide, sodium silicate, sodium metasilicate and ammonium carbonate, and acidulants such as inorganic and inorganic acids, e.g., phosphoric acid, acetic acid, ascorbic acid, citric acid or tartaric acid, hydrochloric acid, and mixtures thereof.

Rheology

The composition may have a viscosity of from 30 mPa·s to 1000 mPa·s. The viscosity is measured at 23° C. using a HAAKE Rotation Viscometer VT 550 with cooling/heating vessel and sensor systems according to DIN 53019 at a shear rate of 12.9 $s^{-1}$. The composition may have a viscosity of from 100 mPa·s to 500 mPa·s, or from 150 mPa·s to 450 mPa·s, or from 200 mPa·s to 400 mPa·s, or from 250 mPa·s to 350 mPa·s. The composition may have a viscosity of from 100 mPa·s to 200 mPa·s. The viscosity range is useful in view of helping to prevent the composition from dripping onto clothes and/or surrounding material. Furthermore, when the viscosity is too high, the composition cannot easily be mixed.

The composition may have a tangent delta of less than 2 at an angular frequency of 1 Hz at 23° C. and at 1% strain. Tangent delta (also known as: tan delta, tan [δ], loss tangent, loss factor) is the ratio of viscous modulus (G") to elastic modulus (G') and is a quantifier of the presence and extent of elasticity in a fluid. How to calculate the tan delta is shown below:

$$G' = \text{Storage Modulus}$$
$$G'' = \text{Loss Modulus}$$
$$\tan \delta = \text{Loss Factor}$$
$$\frac{G''}{G'} = \tan \delta$$
$$|G^*|(w) = G'(w) + iG''(w) = \sqrt{G'^2 + G''^2}$$

Further information on equipment and methodology for calculating tangent delta can be found in the Experimental section below. The composition may have a tangent delta of from 0.6 to 2 at an angular frequency of 1 Hz at 23° C. and at 1% strain. The composition may have a tangent delta of from 0.6 to 1.5, or from 0.6 to 1.0 at an angular frequency of 1 Hz at 23° C. and at 1% strain.

Hair Colouring Agent

The composition may further comprise a hair colouring agent. The hair colouring agent may be a direct dye. The composition may comprise a total amount of from 0.001% to 4%, or from 0.005% to 3%, or from 0.01% to 2% of a direct dye. The presence of a direct dye and the proportion thereof may be useful in that it can provide or enhance colouring/dyeing, particularly with regard to intensity.

The direct dye may be selected from the group consisting of nitro dyes to provide a blue colour, nitro dyes to provide a red colour, nitro dyes to provide a yellow colour, quinone dyes, basic dyes, neutral azo dyes, acid dyes, and mixtures thereof. The direct dye may be a nitro dye to provide a blue colour. The direct dye may be a nitro dye to provide a red colour. The direct dye may be a nitro dye to provide a yellow colour. The direct dye may be a quinone dye. The direct dye may be a basic dye. The direct dye may be a neutral azo dye. The direct dye may be an acid dye.

The direct dye may be selected from the group consisting of Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

Other Features of the Composition of the First Aspect

The composition may comprise one or more radical scavengers, which may be present in a sufficient amount to reduce damage to the hair. The one or more radical scavengers may be advantageously selected such that the one or more radical scavengers are different from an alkalising agent.

The one or more radical scavengers may be selected from the group consisting of: alkanolamines, amino sugars, amino acids, and mixtures thereof. The one or more radical scavengers may be selected from the group consisting of: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan, and potassium, sodium and ammonium salts of the above, and mixtures thereof. The one or more radical scavengers may be selected from the group consisting of: benzylamine, glutamic acid, imidazole, di-tert-butylhydroxytoluene, hydroquinone, catechol, and mixtures thereof. The composition may be substantially free of radical scavenger.

The composition may comprise a chelant. The composition may comprise a chelant in an amount sufficient to reduce the amount of metals available to interact with composition components. Chelants are also known as chelators and chelating agents.

The chelant may be selected from the group consisting of: diamine-N,N'-dipolyacid, monoamine monoamide-N,N'-dipolyacid, and N,N'-bis(2-hydroxybenzyl)ethylenediamine-N,N'-diacetic acid chelants (e.g. EDDS (ethylenediaminedisuccinic acid)), carboxylic acids (e.g. aminocarboxylic acids), phosphonic acids (e g aminophosphonic acids), polyphosphoric acids (in particular straight polyphosphoric acids), salts and derivatives thereof, and mixtures thereof. The chelant may be ethylenediamine tetraacetic acid (EDTA) and/or editronic acid. The chelant may be histidine.

The composition may be substantially free of persulfate.

Exemplary Embodiments of the First Aspect

A composition for providing a film on keratin fibres is provided and comprises:
(a) a film-forming aminosilicone polymer, wherein the aminosilicone polymer comprises amino side chains, and wherein the aminosilicone polymer as a weight average molecular weight of from 10,000 Dalton to 60,000 Dalton;
(b) a silicone resin, wherein the silicone resin is a MQ resin;
(c) a thickening system comprising:
   a deposition enhancer, wherein the deposition enhancer is a hydrophilic and non-ionic polymer, and wherein the deposition enhancer has a weight average molecular weight of from 700,000 Dalton to 3,000,000 Dalton;
   a thickening polymer, wherein the thickening polymer has a weight average molecular weight of at least 10,000 Dalton, and wherein the thickening polymer is a cationic thickening polymer or is a non-ionic thickening polymer; and
(d) a solvent.

The composition may be substantially free of compounds causing precipitation of any component of the composition when the composition is in aqueous solution at pH 5 and at 23° C.

The composition may comprise an ether of a water-soluble polyhydric alcohol; and wherein the composition may comprise one or more pigments having an average $D_{50}$ particle diameter of from 5 micron to 60 micron.

The composition may comprise one or more particulate substances being silica.

A composition for providing a film on keratin fibres may be provided and may comprise:
(a) a film-forming aminosilicone polymer, wherein the aminosilicone polymer comprises amino side chains, and wherein the aminosilicone polymer as a weight average molecular weight of from 10,000 Dalton to 60,000 Dalton;
(b) a silicone resin wherein the silicone resin is a MQ resin;
(c) a thickening system comprising:
   a deposition enhancer, wherein the deposition enhancer is a hydrophilic and non-ionic polymer, and wherein the deposition enhancer has a weight average molecular weight of from 700,000 Dalton to 3,000,000 Dalton;
   a thickening polymer, wherein the thickening polymer has a weight average molecular weight of at least 10,000 Dalton, and wherein the thickening polymer is a cationic thickening polymer or is a non-ionic thickening polymer;
(d) a solvent;
and wherein the composition is substantially free of compounds causing precipitation of any component of the composition when the composition is in aqueous solution at pH 5 and at 23° C.;
and wherein the composition comprises a pigment having an average $D_{50}$ particle diameter of from 5 micron to 60 micron;
and wherein the composition comprises a photoprotective substance.

A composition for providing a pigment-containing film on keratin fibres may be provided and may comprise:
(a) a film-forming aminosilicone polymer, wherein the aminosilicone polymer comprises amino side chains, and wherein the aminosilicone polymer as a weight average molecular weight of from 10,000 Dalton to 60,000 Dalton;
(b) a silicone resin wherein the silicone resin is a MQ resin;
(c) a thickening system comprising:
   a deposition enhancer, wherein the deposition enhancer is a hydrophilic and non-ionic polymer, and wherein the deposition enhancer has a weight average molecular weight of from 700,000 Dalton to 3,000,000 Dalton;
   thickening polymer, wherein the thickening polymer has a weight average molecular weight of at least 10,000 Dalton, and wherein the thickening polymer is a cationic thickening polymer or is a non-ionic thickening polymer; and
(d) a solvent.

The composition may be substantially free of compounds causing precipitation of any component of the composition when the composition is in aqueous solution at pH 5 and at 23° C.

The composition may comprise one or more pigments having an average $D_{50}$ particle diameter of from 5 micron to 60 micron.

A composition for providing a film on keratin fibres may be provided and may comprise:
(a) from 0.1% to 3% of a film-forming aminosilicone polymer, wherein the aminosilicone polymer comprises amino side chains, and wherein the aminosilicone polymer as a weight average molecular weight of from 10,000 Dalton to 60,000 Dalton;
(b) a silicone resin wherein the silicone resin is a MQ resin;
(c) an ether of a water-soluble polyhydric alcohol;
(d) from 0.5% to 10% of a thickening system comprising:
   a deposition enhancer, wherein the deposition enhancer is a hydrophilic and non-ionic polymer, and wherein the deposition enhancer has a weight average molecular weight of from 700,000 Dalton to 3,000,000 Dalton;
   a thickening polymer, wherein the thickening polymer has a weight average molecular weight of at least 10,000 Dalton, and wherein the thickening polymer is a cationic thickening polymer or is a non-ionic thickening polymer;
(e) from 1% to 10% of one or more coloured materials or of one or more pigments;
(f) water;
(g) from 0.1% to 10% of a volatile alcohol, wherein the volatile alcohol has from 1 to 8 carbon atoms and is miscible in water.

The composition may be substantially free of compounds causing precipitation of any component of the composition when the composition is in aqueous solution at pH 5 and at 23° C.

The composition may comprise one or more pigments having an average $D_{50}$ particle diameter of from 5 micron to 60 micron;
optionally wherein the one or more pigments are selected from the group consisting of iron oxide, titanium dioxide, mica, borosilicate, and combinations thereof.

$2^{nd}$ Aspect

The second aspect relates to a method for providing a film comprising pigment or coloured material onto keratin fibres, the method comprising applying the as set out herein above onto keratin fibres and allowing the keratin fibres to dry or drying them. The method may comprise applying the composition as set out herein above onto keratin fibres and then drying them with a device selected from the group consisting of blow dryer, heated irons, heated hood, and combinations thereof.

The drying may be carried out using a hair dryer or a drying hood. The drying may be carried out at a temperature from 28° C. to 40° C. The temperature may be useful in that it assists in the evaporation of solvent and other volatile compounds and thus allows excellent film formation. The method may comprise drying the keratin fibres with a device selected from the group consisting of blow dryer, heated irons, heated hood, and combinations thereof.

The method may comprise applying a composition as set out herein above onto keratin fibres and allowing the keratin fibres to dry or drying them; and subsequently, applying a formulation comprising a silicone resin onto keratin fibres and allowing the keratin fibres to dry or drying them. The composition may comprise a white pigment or a black pigment.

The method may comprise applying a first composition as set out herein above onto keratin fibres and allowing the keratin fibres to dry or drying them; and subsequently, applying a second composition as set out herein above onto keratin fibres and allowing the keratin fibres to dry or drying them; wherein the first composition may comprise a first pigment exhibiting a first colour and the second composition may comprise a second pigment exhibiting a second colour. The first colour is white or black. The second colour may be neither white nor black. The first pigment may comprise titanium dioxide or carbon.

The method may not encompass or include bleaching the hair.

3$^{rd}$ Aspect

A kit is provided and comprise: the composition as set out herein above; optionally a formulation comprising one or more pigments and/or one or more coloured materials; and an applicator. The kit may consist of a packaging comprising the composition as set out herein above and a sponge head; and wherein the composition may comprise one or more pigments and/or one or more coloured materials. The kit may comprise a multi-compartment package comprising a first compartment and a second compartment; wherein the first compartment may comprise the composition as set out herein above and the second compartment may comprise the one or more pigments and/or the one or more coloured materials.

The kit may comprise a first composition as set out herein above comprising a first pigment and a second composition as set out herein above comprising a second pigment; wherein the first pigment and the second pigment may exhibit different colours.

4$^{th}$ Aspect

A fourth aspect relates to the use of the kit according to the 3$^{rd}$ aspect for applying pigment and/or coloured material to keratin fibres.

EXAMPLES

The following examples further describe and demonstrate embodiments within the scope of the present invention. The examples are given solely for the purpose of illustration, and are not to be construed as limitations of the present invention since many variations thereof are possible without departing from its scope.

Composition Examples

| Ingredient | Example | | | | | | | | | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11 | 12 |
| BELSIL ADM 8301 E[1] | 10 | 8 | 12 | 15 | 14 | 18 | 15 | 14 | 12 | 15 | 15 | 15 |
| Salcare ® SC 96[2] | 0.6 | 0.75 | 0.75 | 0.75 | — | 0.75 | 0.75 | — | 0.75 | 0.6 | 0.5 | 0.75 |
| 2-hydroxyethyl cellulose[3] | — | — | — | — | 0.2 | — | — | — | — | — | — | — |
| Xanthan gum[4] | — | — | — | — | — | — | — | 0.3 | — | — | — | — |
| PEG-45M[5] | 0.2 | 0.3 | — | — | 0.1 | 0.2 | 0.2 | — | — | 0.2 | 0.2 | 0.2 |
| PEG-23M[6] | — | — | 0.2 | — | — | — | — | — | 0.2 | — | — | — |
| PEG-90M[7] | — | — | — | 0.1 | — | — | — | — | — | — | — | — |
| PEG-7M[8] | — | — | — | — | 0.3 | — | — | — | — | — | — | — |
| PEG-180M[9] | — | — | — | — | — | — | — | 0.1 | — | — | — | — |
| Tergitol[$] | — | 0.5 | — | 0.5 | — | — | 0.5 | — | 0.5 | 0.5 | 0.5 | 0.5 |
| Pigment[§] | 5.0 | 5.0 | 5.0 | — | 5.0 | 5.0 | 5.0 | 5.0 | 5.0 | 5.0 | 5.0 | 5.0 |
| Aquasolved[#] | — | — | — | 2.5 | 2.5 | — | — | 2.3 | — | — | — | — |
| Ethanol | 1.0 | 1.5 | 2.0 | — | — | 1.0 | 1.5 | 2.0 | — | 1.0 | 1.0 | 1.0 |
| Preservative* | 1.0 | 2.0 | 1.5 | 0.5 | 1.0 | — | — | — | 1.0 | 1.0 | 1.0 | 1.0 |
| Perfume | — | 0.1 | 0.07 | 0.1 | — | — | — | 0.2 | 0.2 | 0.1 | 0.1 | 0.1 |
| Deionised water | QSP | QSP | QSP | QSP | QSP | QSP | QSP | QSP | QSP | QSP | QSP | QSP |

KEY:

[1]= from Wacker, aqueous mixture of poly[3-((2-aminoethyl)amino)propyl]methyl(dimethyl)siloxane (hydroxyterminated), octamethylcyclotetrasiloxane, MQ resin, ethylene glycol monohexyl ether and diethyleneglycol monobutylether;

[2]= Salcare ® SC 96 from BASF, which has the INCI name: Polyquaternium-37 (and) Propylene Glycol Dicaprate Dicaprylate (and) PPG-1 Trideceth-6;

[3]= Cellosize ™ HEC QP 4400 from Dow;

[4]= Keltrol ® from Kelco or Natrosol ® 250 HHR from Herkules;

[5]= POLYOX WSR N-60K from Dow has formula $H(OCH_2CH_2)_nOH$ wherein n is an integer and where n has an average value of 45,000 and the weight average molecular weight is 2,000,000 Dalton;

[6]= POLYOX WSR N-12K from Dow has the formula $H(OCH_2CH_2)_nOH$ wherein n is an integer with an average value of 23,000 and the weight average molecular weight is 1,000,000 Dalton;

[7]= POLYOX WSR-301 from Dow has the formula $H(OCH_2CH_2)_nOH$ wherein n is an integer with an average value of 90,000 and the weight average molecular weight is 4,000,000 Dalton;

[8]= POLYOX N-750 from Dow has the formula $H(OCH_2CH_2)_nOH$ wherein n is an integer with an average value of 7,000 and the weight average molecular weight is 300,000 Dalton;

[9]= POLYOX WSR-308 from Dow, as formula $H(OCH_2CH_2)_nOH$ wherein n is an integer and where n has an average value of 180,000 and has a weight average molecular weight of 8,000,000 Dalton;

[$]= C11-15 Pareth-9 and is the polyethylene glycol ether of a mixture of synthetic C11-15 fatty alcohols with an average of 9 moles of ethylene oxide.

*= 2-phenoxyethanol and/or phenylmethanol;

[#]= from Firmenich;

[§]= pigment selected from: mica and/or iron oxides; Colorona Bronze Fine; SynCrystal Almond; Xirona Le Rouge; DUOCROME RV 524C; SynCrystal Jade; Colorona Precious Gold; Ronastar Red; Syncrystal Sapphire; Impact Silver Rutile; KTZ Misterioso Pewter; and combinations thereof.

Experimental

Dripping Test

Various compositions are tested in order to elucidate advantageous dripping behaviour of various thickening systems. A base composition is prepared that comprises water, an aminosilicone polymer (polydimethylsiloxane polymer having graft amino groups), silicone resin (MQ resin), and mixture of diethyleneglycol monobutylether and ethylene glycol monohexyl ether. As per the below table, a deposition enhancer or a thickening polymer is added to the base composition in the amounts (wt %) indicated. 0.5 g of pigment is then added to 9.5 g of this composition. The composition is applied to hair and the dripping behaviour observed and, where relevant, the number of drips in 30 seconds counted.

| | Deposition enhancer | Thickening polymer | Visual observations on consistency | Dripping test |
|---|---|---|---|---|
| 1 | — | — | Watery | 15 drips in 30 s |
| 2 | — | 1 * | Creamy | No dripping |
| 3 | — | 0.5 # | Creamy | No dripping |
| 4 | 1 § | — | Gel-like, sticky | No dripping |
| 5 | — | 0.8 # | Creamy | No dripping |
| 6 | 0.2 β | — | Watery, stringy | 2 drips in 30 s |
| 7 | 0.2 § | — | Watery | 2 drips in 30 s |

Key:
* = ™HEC QP 4400 from Dow (Hydroxyethylcellulose);
# = Salcare SC 96 from BASF;
β = POLYOX WSR 308 (Dow), which has a M. Wt. of 8 million Dalton;
§ = Polyox WSR N60K (Dow), which has a M. Wt. of 2 million Dalton.

Conclusions: Compositions 2 and 3 performed the best. When comparing compositions 6 and 7, it is apparent that the higher weight average molecular weight of the deposition enhancer caused composition stringiness. Composition 4 demonstrates that deposition enhancer alone does not provide the preferred creamy consistency. Only the compositions comprising a thickening polymer exhibited the preferred creamy consistency.

Rheology

The following compositions are prepared.

| | Water | Pigment§ | Z | EtOH | Thickening polymer* | Deposition enhancer# | Phenoxyethanol | Total |
|---|---|---|---|---|---|---|---|---|
| A | 85 | 0 | 15 | 0 | 0 | 0 | 0 | 100 |
| B | 77.3 | 5 | 15 | 1 | 0.75 | 0 | 1 | 100 |
| C | 77.8 | 5 | 15 | 1 | 0 | 0.2 | 1 | 100 |
| D | 77.6 | 5 | 15 | 1 | 0.25 | 0.2 | 1 | 100 |
| E | 77.3 | 5 | 15 | 1 | 0.5 | 0.2 | 1 | 100 |
| F | 77.1 | 5 | 15 | 1 | 0.75 | 0.2 | 1 | 100 |
| G | 76.8 | 5 | 15 | 1 | 1 | 0.2 | 1 | 100 |

KEY:
Z = Wacker ® HC303 (as per BELSIL ADM 8301 E above commercially available);
EtOH = ethanol;
*= Salcare ® SC96 from BASF;
= PEG-45M (Polyox WSR N-60K) from Dow;
§= copper pigment.

The viscosity of these compositions is measured and an average calculated. A simple flow viscosity experiment provides information on how fast the same quantity of composition flows down the same gradient and all other conditions equal. The dripping test is as per above.

| | Viscosity* | | | | Flow viscosity | |
|---|---|---|---|---|---|---|
| | 1 | 2 | 3 | Average | (cm/s) | Dripping test |
| A | 1.9 | 2.85 | 2.85 | 2.53 | 3.1 | 1 |
| B | 100 | 99.9 | 100 | 99.96 | 2.1 | 0 |
| C | 9.51 | 8.56 | 8.56 | 8.87 | 7.6 | 0 |
| D | 45.6 | 44.7 | 43.7 | 44.66 | 3.6 | 0 |
| E | 124 | 123 | 122 | 123 | 2.2 | 0 |
| F | 319 | 318 | 317 | 318 | 1.5 | 0 |
| G | 757 | 755 | 756 | 756 | 1 | 0 |

KEY:
*viscosity in mPa · s using a Haake viscometer (64.50 1/s) MV DIN with 5 minute conditioning time.

Consequently, compositions B and D to G fall within the viscosity scope claimed i.e. viscosity of from 30 mPa·s to 1000 mPa·s. Composition D has the lowest viscosity out of compositions B and D to G. Composition D has the fastest flow viscosity out of compositions B and D to G. Composition G has the highest viscosity and also the slowest flow viscosity.

The time-dependent viscoelastic properties in the linear viscoelastic region with an amplitude sweep are measured and compared. The storage modulus and tangent delta are measured using a TA-Instruments AR2000ex rheometer. In this experiment, different compositions are compared. The components of the composition are mixed together, and then homogenised using an IKA KS 501 digital at 160 rpm and then loaded it onto the rheometer. The rheometer is used with the following specifications/conditions: upper geometry, 60 mm steel; lower geometry, Peltier Element; temperature, 23° C.; Pre-shear, 5 1/s, 1 min; equilibration, 2 min; normal force, off; gap: 650 μm. An amplitude sweep (strain sweep) was carried out with a strain of between 0.05% and 50%, with log data sampling (10 points/decade) and at a frequency of 1 Hz (6.283 rad/s).

These data are depicted in FIG. 1, which is also summarised in the below table.

| Composition | Symbol in Fig | Thickening polymer* | Deposition enhancer# | Tangent delta (at 1 Hz and 1% strain) |
|---|---|---|---|---|
| B | ▲ triangle | 0.75 | 0 | is less than 2 but greater than 0.6 |
| D | ✗ cross | 0.25 | 0.2 | is greater than 2 |
| E | ◆ diamond | 0.5 | 0.2 | is greater than 2 |
| F | ✚ plus | 0.75 | 0.2 | is less than 2 but greater than 0.6 |
| G | ○ circle | 1 | 0.2 | is less than 2 but greater than 0.6 |

KEY:
*= Salcare ® SC96 from BASF;
= PEG-45M (Polyox WSR N-60K) from Dow.

Consequently, compositions D and E do not have a tangent delta of less than 2 at an angular frequency of 1 Hz at 23° C.

Coating Step

The same composition pursuant to the present invention is tested for the performance effects of post-treatment. In the application columns the events proceed from left to right i.e. first a composition was applied to dry hair. The performance is then assessed visually versus a reference treatment, which is experiment 2.

| | Application | | | | Performance versus 2 | | |
|---|---|---|---|---|---|---|---|
| Composition* | Combing | Blow dry | Coating formulation | Blow dry | Wash fastness | Rub off | Visual effect |
| 1 Yes | — | Yes | — | — | slightly better | worse | more intense |
| 2 Yes | — | Yes and with combing | — | — | equal | equal | equal |
| 3 Yes | Yes | Yes | — | — | equal | worse | equal |
| 4 Yes | Yes | Yes and with combing | — | — | worse | slightly better | obvious less intense |
| 5 Yes | — | Yes | Yes | Yes | equal | equal | equal |
| 6 Yes | — | Yes | Yes | Yes and with combing | equal | equal | more intense |
| 7 Yes | Yes | Yes | Yes | Yes | slightly worse | equal | equal |
| 8 Yes | Yes | Yes | Yes | Yes and with combing | slightly worse | slightly worse | slightly less intense |
| 9 Yes | — | Yes and with combing | Yes | Yes | equal | equal | slightly more intense |
| 10 Yes | — | Yes and with combing | Yes | Yes and with combing | equal | worse | slightly more intense |
| 11 Yes | Yes | Yes and with combing | Yes | Yes | equal | worse | less intense |
| 12 Yes | Yes | Yes and with combing | Yes | Yes and with combing | slightly better | slightly worse | slightly less intense |
| 13 Yes | Yes | — | Yes | Yes | better | slightly worse | slightly less intense |
| 14 Yes | Yes | — | Yes | Yes and with combing | slightly better | slightly better | equal |
| 15 Yes | — | — | Yes | Yes | equal | equal | equal |
| 16 Yes | — | — | Yes | Yes and with combing | equal | slightly worse | equal |

KEY:
*= pursuant to the present invention.

It can thus be concluded that experiment 14 performed the best overall. Experiments 6 and 9 were also very good. Experiments 5 and 15 were equal to the reference. The reference was a treatment with the composition according to the present invention and then blow drying with combing.

The best result was achieved in experiment 14 where the composition according to the present invention is applied to the hair and then combed followed by the coating step and then blow drying with combing.

Color and Hair Performance: Influence of the MQ Resin

The following compositions were prepared (all amounts are in wt %). A composition H comprises a MQ resin while a comparative composition I does not comprise a MQ resin. The comparative composition I is not within the scope of the present invention.

| | Water | Pigment§ | Z | W | EtOH | Thickening polymer* | Deposition enhancer# | Phenoxy-ethanol | Anti-freeze agent$ | Total |
|---|---|---|---|---|---|---|---|---|---|---|
| H | Qsp | 5 | 15 | 0 | 2 | 0.75 | 0.2 | 1 | 0.5 | 100 |
| I | Qsp | 5 | 0 | 15 | 2 | 0.75 | 0.2 | 1 | 0.5 | 100 |

KEY:
Z = Wacker ® HC303 (commercially available);
W = Wacker ® HC303 as set out herein above without any MQ resin;
EtOH = ethanol;
*= Salcare ® SC96 from BASF;
= PEG-45M (Polyox WSR N-60K) from Dow;
§= copper pigment from Colorona ®; and
$= $C_{11-15}$ Pareth-9 and is the polyethylene glycol ether of a mixture of synthetic C11-15 fatty alcohols with an average of 9 moles of ethylene oxide.

Hair Strands

Caucasian Hair color 4/0 Euro-Natural-Hair

Hair strands having a width of 1.5 cm and a length of 10 cm.

Available from Kerling International Haarfabrik

Application of Each of the Compositions H or I on Hair Strands 1.0 g of a composition H or a comparative composition I was applied on 1.0 g of hair strands. The respective composition H or I was distributed into the hair strands with the help of a brush or a sponge head. The hair strands were flipped. The respective composition H or I was further distributed until all hair fibers of the hair strands were completely and evenly colored.

Each treated hair strand was blow dried manually with a conventional blow dryer for 2 minutes. After each 30 seconds, the treated hair strands were combed from the top to the bottom of the hair strands.

Visual Assessment of the Color Effect/Intensity:

The hair strands treated with the composition H were compared to the hair strands treated with the comparative composition I under a D65 light box. The assessment was rated as follows:

| −3 | −2 | −1 | 0 | 1 | 2 | 3 |
|---|---|---|---|---|---|---|
| Obvious worst | Noticeable worst | Slightly worst | Equal | Slightly better | Noticeable better | Obvious better |

The reference was a non-treated hair strand.

Hair strands treated with the composition H exhibited a noticeable better effect on hair than the reference.

Hair strands treated with the comparative composition I exhibited a slight worst effect on hair than the reference.

When the composition comprises a MQ resin, the color effect on hair is better noticeable than when the composition does not comprise a MQ resin.

Effect of Hair Wash

The hairs strand treated with the respective composition H or I were washed for 30 seconds with water then 30 seconds with 0.5 mL of Wella Professionals Brilliance Shampoo, and then 30 seconds with water.

Each treated hair strand was blow dried manually with a conventional blow dryer for 2 minutes. After each 30 seconds, the treated hair strands were combed from the top to the bottom of the hair strands.

The hair strands treated with the composition H showed a good pigment adhesion to the hair, by visual assessment. However, the hair strands treated with the comparative composition I only showed a slight pigment adhesion to the hair, by visual assessment.

Hair Feel

The hair strands treated with the respective composition H or I were pulled through thumb and index fingers. The treated hair strands were assessed versus an untreated hair strand.

The hair strands treated with the composition H showed a noticeable coated effect. However, the hair strands treated with the comparative composition I only showed a slight coated effect.

Water Dipping Test

The hair strands treated with the respective composition H or I were dipped for 15 times for 15 seconds in 200 mL of distillate water. A picture was taken after the pigments have sedimented. It has been observed that the hair strands treated with the composition H lost few pigments. However, the hair strands treated with the comparative composition I lost much more pigments versus the hair strands treated with the composition H.

CONCLUSION

When the hair strands are treated with the composition H which comprises a MQ resin, versus the comparative composition I, the treated hair strands exhibited an improved colored performance, with an increased pigment adhesion on hair, and a better resistance to wash fastness.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for providing a film on keratin fibres, the composition comprising:
   (a) a film-forming aminosilicone polymer, the aminosilicone polymer having the structure according to Formula I:

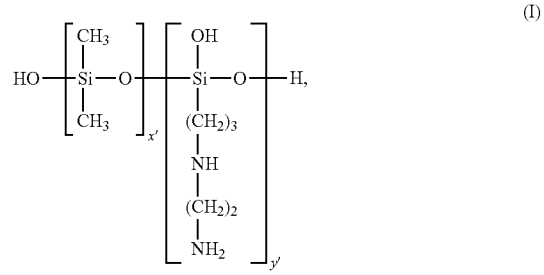

wherein x' and y' are positive integers, such that a weight average molecular weight of the aminosilicone polymer is from 10,000 Dalton to 60,000 Dalton;
   (b) a silicone resin wherein the silicone resin is a MQ resin;
   (c) a thickening system, in a range of from about 0.5% to about 2% of the composition, the thickening system comprising a thickening polymer and a deposition enhancer, wherein the deposition enhancer is polyethylene glycol-45 in 0.2% of the thickening system and the thickening polymer is polyquaternium-37 in a range of from 0.75% to 1% of the thickening system; and (d) a solvent, one or more pigments, wherein the one or more pigments have a $D_{50}$ particle diameter of from about 5 micron to about 60 micron, wherein, the composition has a viscosity of from about 50 mPa·s to about 1000 mPa·s, wherein the viscosity is measured at about 23° C., and the composition has a tangent delta of less than 2 at an angular frequency of 1 Hz at 23° C. and at 1% strain.

2. The composition of claim 1, wherein the composition comprises water.

3. The composition of claim 1, wherein the composition comprises one or more coloured materials, wherein the one or more coloured materials are selected from the group consisting of coloured fibres, coloured beads, nano-particles, coloured polymers comprising covalently attached dyes, and combinations thereof.

4. The composition of claim 1, wherein the composition has a pH, wherein the pH of the composition is from about 3.0 to about 11.0.

5. The composition of claim 1, wherein the composition comprises from about 1% to about 15% of the aminosilicone polymer (a), by total weight of the composition.

6. A method for providing a film comprising pigment or coloured material onto keratin fibres, the method comprising applying the composition of claim 1 onto keratin fibres and allowing the keratin fibres to dry or drying them.

\* \* \* \* \*